United States Patent [19]
Baker et al.

[11] Patent Number: 6,018,060
[45] Date of Patent: Jan. 25, 2000

[54] MEMBRANE PROCESS AND APPARATUS FOR ARGON PURGING FROM OXIDATION REACTORS

[75] Inventors: Richard W. Baker, Palo Alto; Douglas Gottschlich, Mountain View, both of Calif.

[73] Assignee: Membrane Technology and Research, Inc., Menlo Park, Calif.

[21] Appl. No.: 09/166,342

[22] Filed: Oct. 5, 1998

Related U.S. Application Data

[63] Continuation-in-part of application No. 08/890,856, Jul. 19, 1997, Pat. No. 5,817,841.

[51] Int. Cl.⁷ .......................... C07D 303/00; C07C 45/28; C07C 45/34
[52] U.S. Cl. .......................... 549/513; 568/397; 568/398; 568/409
[58] Field of Search .................... 568/397, 398, 568/409; 549/513

[56] References Cited

U.S. PATENT DOCUMENTS

| | | | |
|---|---|---|---|
| 3,444,189 | 5/1969 | Olivier | 260/497 |
| 3,547,983 | 12/1970 | Mottern et al. | 260/488 |
| 3,557,191 | 1/1971 | Copelin | 260/497 |
| 4,553,983 | 11/1985 | Baker | 55/16 |
| 4,857,078 | 8/1989 | Watler | 55/16 |
| 4,879,396 | 11/1989 | Ozero | 549/534 |
| 4,904,807 | 2/1990 | Ozero | 549/534 |
| 4,906,256 | 3/1990 | Baker et al. | 55/16 |
| 4,963,165 | 10/1990 | Blume et al. | 53/22 |
| 4,994,094 | 2/1991 | Behling et al. | 55/16 |
| 5,032,148 | 7/1991 | Baker et al. | 55/16 |
| 5,069,686 | 12/1991 | Baker et al. | 55/16 |
| 5,127,926 | 7/1992 | Baker et al. | 55/16 |
| 5,179,215 | 1/1993 | Ramachandran et al. | 549/262 |
| 5,278,319 | 1/1994 | Ramachandran et al. | 549/249 |
| 5,281,255 | 1/1994 | Toy et al. | 95/50 |
| 5,501,722 | 3/1996 | Toy et al. | 95/50 |

*Primary Examiner*—Ba K. Trinh
*Attorney, Agent, or Firm*—J. Farrant

[57] ABSTRACT

A process and apparatus for manufacture of organic products, particularly chemical intermediates, by oxidation of organic feedstocks. A membrane unit containing a membrane selectively permeable to the organic over argon is used to recover the feedstock from the argon purge stream.

28 Claims, 7 Drawing Sheets

MEMBRANE PROCESS AND APPARATUS FOR ARGON PURGING FROM OXIDATION REACTORS

This is a continuation-in-part application of application Ser. No. 08/890,856, filed Jul. 10, 1997, now U.S. Pat. No. 5,817,841.

FIELD OF THE INVENTION

The invention relates to manufacture of chemical intermediates by oxidation of organic feedstocks, and in particular to using a membrane unit to treat off-gas streams from the oxidation reaction zone to purge argon gas without losing large amounts of the organic feedstocks.

BACKGROUND OF THE INVENTION

A large number of chemical products, particularly chemical intermediates, are produced by selective, catalytic oxidation of an appropriate organic feedstock. One of the most important intermediates produced in this manner is ethylene oxide, which is made by oxidation of ethylene in the presence of a silver catalyst. The process operates in a loop, with modest conversion per pass, so that large amounts of unreacted ethylene are recirculated back to the reaction zone at each pass. The raw gas from the reactor is usually scrubbed with water to remove the ethylene oxide product before the gas is recirculated.

Similar processes are carried out in the manufacture of a number of other chemical products, where an oxidation reactor is used in a multiple-pass, loop mode, and where avoidance of build-up of an inert gas, particularly argon or nitrogen, in the reactor loop requires continuous or occasional purging. Examples of materials produced by selective oxidation include, but are not limited to:

Acetaldehyde, vinyl acetate and vinyl chloride, produced directly or indirectly from ethylene
Propylene oxide and acrylonitrile, produced from propylene
Benzoic acid, produced from toluene
Caprolactam, produced from cyclohexane
Maleic acid, maleic anhydride and phthalic anhydride, produced from various aromatic feedstocks
Phenol, produced from cumene
Terephthalic acid and dimethyl terephthalate, produced from p-xylene.

The manufacture of acrylonitrile involves the reaction of propylene with ammonia and oxygen (usually from air), in the presence of a suitable catalyst, such as an oxide of bismuth, molybdenum, iron, nickel, or cobalt. The reactor off-gases are scrubbed, producing an aqueous acrylonitrile stream, which passes to further recovery and purification processes, typically steam-stripping and distillation. Scrubber off-gases are vented or recycled for recovery of the propylene.

Propylene oxide is manufactured by a two-stage process. The first is an epoxidation reaction of iso-butane and oxygen. The resulting tert-butyl hydroperoxide-butyl alcohol is reacted with propylene in the presence of a suitable catalyst, typically a molybdenum compound. The reaction mixture is separated and the crude product purified by distillation. The unreacted propylene is recycled for reuse.

Phthalic anhydride is produced by mixing o-xylene with compressed air and passing the mixture into a reactor containing a vanadium oxide or titanium-antimony oxide catalyst. The reactor off-gas is condensed, and the crude phthalic anhydride is purified under vacuum distillation.

Benzoic acid is produced by liquid phase oxidation of toluene in a stirred tank reactor, using cobalt naphthenate as catalyst. The reaction liquids are fractionated, and the crude product is rectified and further purified if necessary. Toluene is recycled from the fractionation step to the reactor.

Manufacture of phenol is a two-step process, first reacting cumene and sodium carbonate with oxygen in air to produce a cumene hydroperoxide. The crude hydroperoxide and a dilute acid are fed to a cleavage reactor, which produces phenol and an acetone by-product. The phenol is distilled and purified. Cumene from the first reactor is recycled back to the process.

Terephthalic acid (TPA) is produced in a similar manner to benzoic acid, by liquid phase oxidation of p-xylene using a cobalt salt catalyst. The reaction is carried out in an acetic acid solution, causing the TPA product to form a slurry at the base of the reactor. The reacted mixture is subjected to flash evaporation to remove the unreacted xylene and acetic acid, and the TPA slurry is centrifuged, crystallized and dried.

Dimethyl terephthalate (DMT) is made by the esterification of TPA with methyl alcohol to produce crude DMT, which is oxidized and distilled. Alternatively, DMT may be produced directly by a two-step process, first reacting p-xylene and recycled by-product p-methyl toluate in the presence of air and a catalyst. The intermediate product is mixed with methyl alcohol in an esterification tower. The resulting crude DMT is crystallized and distilled.

Caprolactam is also manufactured in a two-step process, first by a combustion reaction of sulfuric acid and ammonia. The resultant nitrosylsulfuric acid is reacted with hydrogen chloride and bubbled through cyclohexane in a photoreactor to form a crude caprolactam product. The crude product is further separated and treated to produce aqueous caprolactam. Cyclohexane is recovered from the separation step and recycled to the process.

Vinyl acetate is formed by the reaction of ethylene, acetic acid, and oxygen in the presence of a palladium salt or other suitable catalyst. The crude product is purified, and any unreacted ethylene is recycled to the reactor. The use of a membrane process for argon purging and organic recovery from vinyl acetate reactors is described in patent application (not yet assigned), incorporated herein by reference in its entirety.

Yet another related process is the oxychlorination of ethylene, in which ethylene, oxygen and hydrogen chloride are reacted in the presence of a fluid catalyst to produce ethylene dichloride. The reaction products are sent to a condensation step where the ethylene dichloride and water are removed. A portion of the remaining gas must then be purged and/or treated to remove excess argon, nitrogen, carbon dioxide and carbon monoxide before recirculation to the reactor.

Oxidation processes were originally developed using air as the oxygen source, but many modern processes operate with a feed of oxygen-enriched air or high-purity oxygen. The use of pure oxygen typically increases yields and reduces or eliminates the need for nitrogen purging from the process loop, since much less inert gas is fed into the loop initially.

Even when oxygen-oxidation is used, however, some purging is necessary. This is because "pure" oxygen is typically slightly less than 100% pure. The most significant other component is argon, with a typical concentration of about 1%. Argon is present in air and, since argon and oxygen have close boiling points, is not well separated in the cryogenic distillation process used to produce oxygen from air.

If argon is not removed, it builds up in the reactor loop, and can adversely affect the reaction dynamics and the flammability of the gas mixture, and/or reduce the life of the catalyst. Therefore, selective oxidation processes normally provide for a small purge stream to be withdrawn from the loop, usually after the crude product has been scrubbed out or otherwise separated. In addition to argon, the purge gas typically contains unreacted organic feedstock, oxygen, carbon dioxide, nitrogen, and small amounts of hydrocarbons and other contaminants. If methane has been added to the reaction zone to control the flammability of the gas mixture, methane may also be present in the purge gas. In prior art processes, this stream is incinerated or used as boiler fuel.

Although the volume of the purge stream is small, its destruction may result in the loss, from a typical plant, of many pounds of organic feedstock for every ton of chemical produced. In large-scale chemical intermediate processes such as those listed above, even incremental improvements in efficiency can affect process economics significantly. Therefore, a process that can reduce or eliminate this loss of organic feedstock would be valuable to the industry.

Patents that describe chemical intermediate manufacture by oxidation of organic feedstocks include: U.S. Pat. No. 5,179,215, to BOC, which discusses the manufacture of petrochemicals by selective oxidation and teaches the use of pressure or temperature swing adsorption to recover unreacted hydrocarbon feedstock. U.S. Pat. No. 5,278,319, also to BOC, further discusses the manufacture of petrochemicals by selective oxidation and teaches the use of a carbon dioxide removal system that also removes excess carbon monoxide. The hydrocarbon feedstock, now with the desired amount of carbon monoxide in the mix, may be recycled to the oxidation reactor.

A specific oxidation process, vinyl acetate manufacturing, is discussed in U.S. Pat. No. 3,444,189, to Union Oil Co., which describes the synthesis of vinyl acetate by oxidation of ethylene and acetic acid. Other references that teach the general manufacturing process for vinyl acetate include U.S. Pat. No. 3,557,191, to DuPont, which describes a process that uses ethylene to produce acetic acid, which is then reacted with additional ethylene to produce vinyl acetate. U.S. Pat. No. 3,547,983, to Air Reduction Co., Inc., describes the use of ethane instead of ethylene in the production of vinyl acetate.

Separation of certain gas mixtures by means of selective membranes has been known to be possible for many years, and membrane-based gas separation systems are emerging to challenge conventional separations technology in a number of areas. That membranes have the potential to separate organic vapors from other gases is also known. For example, U.S. Pat. Nos. 4,553,983; 4,857,078; 4,963,165; 4,906,256; 4,994,094; 5,032,148; 5,069,686; 5,127,926; 5,281,255 and 5,501,722 all describe membranes, systems or processes suitable for such separations.

U.S. Pat. No. 4,879,396, to Ozero, discloses a process for removing both carbon dioxide and argon from an ethylene oxide reactor loop by means of an argon-selective membrane, that is, a membrane that preferentially permeates argon and retains ethylene. U.S. Pat. No. 4,904,807, also to Ozero, discloses a process for removing argon from the reactor loop by means of an argon-selective membrane. In both cases, because the membrane is not perfectly selective, a portion of the ethylene is lost inevitably with the argon vent stream.

SUMMARY OF THE INVENTION

The invention is a process and apparatus for producing organic chemical products that provides a new and advantageous technique for venting excess argon from the reaction loop with reduced loss of organic feedstock.

In its basic form, the process of the invention comprises:
(a) performing one or more reaction steps in a reaction zone to form an organic product, at least one of the reaction steps comprising a reaction of an organic feedstock and oxygen;
(b) withdrawing from the reaction zone a crude organic product stream comprising the organic product, the organic feedstock and argon;
(c) removing at least a portion of the crude product stream to form a non-product stream;
(d) providing a membrane having a feed side and a permeate side, and being selectively permeable to the organic feedstock over argon;
(e) passing at least a portion of the non-product stream across the feed side under conditions in which there is a pressure drop from the feed side to the permeate side;
(f) withdrawing from the feed side an argon-rich purge stream enriched in argon and depleted in the organic feedstock compared with the non-product stream;
(g) withdrawing from the permeate side an organic-feedstock-rich permeate stream enriched in the organic feedstock and depleted in argon compared with the non-product stream;
(h) recirculating at least a portion of the organic-feedstock-rich permeate stream to the reaction zone.

Step (a), the reaction step or steps to form an organic product, may be carried out in any known manner, such as by using an air-oxidation process or an oxygen-oxidation process in the presence of an appropriate catalyst. Depending on the specifics of the organic product being produced and the reaction process(es) used, the raw gas mixture withdrawn from the reaction zone typically contains the organic product, organic feedstock, oxygen, carbon dioxide, carbon monoxide, nitrogen, argon, water vapor and minor amounts of other components. If an air-oxidation process is used, the gas will obviously contain large amounts of nitrogen; if an oxygen-oxidation process is used, methane may be added to raise the flammability limit of the feed gas and can be present in the raw gas.

The organic product may be removed from the raw gas exiting the reaction zone, as specified in step (c), by any convenient technique. Absorption of the organic product into water is typical in many chemical processes, leaving a scrubbed non-product off-gas stream. Other processes employ, for example, flash evaporation or condensation, both of which produce an off-gas stream of unreacted organic feedstock and contaminants. In prior art processes, a small amount of the off-gas stream is purged to remove argon, as explained in the Background section above. The remainder, or at least a portion of the remainder, is typically further treated to remove carbon dioxide and/or carbon monoxide, and then recirculated to the reaction zone.

In the process of the invention, a portion of the scrubbed non-product gas stream is passed to a membrane unit. The unit contains a membrane, preferably a rubbery membrane, that is selectively permeable to the organic feedstock compared with argon; that is, it permeates the organic feedstock faster than argon.

The membrane separation process may be configured in many ways, and may include a single bank of membrane modules or an array of two or more banks in multi-stage or multi-step arrangements.

A driving force for permeation across the membrane is usually provided by maintaining a pressure difference between the feed and permeate sides. This can be accomplished in a variety of ways.

Since the membrane is selectively permeable to the organic feedstock, the residue stream leaving the feed side of the membrane is enriched in argon and depleted in organic compared with the feed stream to the membrane. It is possible to remove from the membrane feed stream, that is, to recover into the membrane permeate stream, a chosen percentage, such as 30%, 40%, 50%, 60%, 70%, 80%, 90%, 95% or even 99% of the organic that would otherwise be vented and lost. The amount of organic removed can be controlled by varying the stage-cut at which the membrane unit operates, as explained in the Detailed Description below. To achieve good organic recovery, it is preferred that the membrane unit be operated at a stage-cut of at least about 30%, more preferably at least about 50% and most preferably higher. Thus, the residue stream can be vented to control argon content in the reaction zone with little loss of organic. The organic feedstock, which has been captured in the permeate stream, may be recirculated directly or indirectly to the reaction zone.

As in many of the prior art processes, carbon dioxide as well as argon usually must be removed from the reactor off-gas to control carbon dioxide build-up in the reaction zone. This may be done by any convenient method. The carbon dioxide removal step may be carried out on a separate portion of the scrubbed off-gas stream, may be carried out on the permeate stream following the removal of argon by the membrane separation step, or may be carried out upstream of the membrane separation step, for example. This flexibility represents a further advantage of the invention. Since it is generally, although not necessarily, the case that the organic-feedstock-enriched stream will be returned to the reactor loop, this recirculation of part of a stream that was previously vented from the loop can be used to adjust the reaction characteristics to some extent.

In another aspect, the invention is apparatus for chemical intermediate manufacture, including a reaction zone, an organic product recovery and purification train, an optional carbon dioxide removal unit, and a membrane unit, containing a membrane selectively permeable to the organic over argon, for argon removal.

In yet another aspect, the invention is a process for treating an argon purge stream to vent argon and recapture organic feedstock.

It is an object of the invention to improve organic chemical product manufacturing processes that use selective oxidation.

It is an object of the invention to provide a process for removing argon from selective oxidation reaction zone vent streams.

It is an object of the invention to provide a process for removing argon from selective oxidation reaction zone vent streams with minimal corresponding loss of organic feedstock.

Other objects and advantages of the invention will be apparent from the description of the invention to those of ordinary skill in the art.

DETAILED DESCRIPTION OF THE INVENTION

Figure 1:
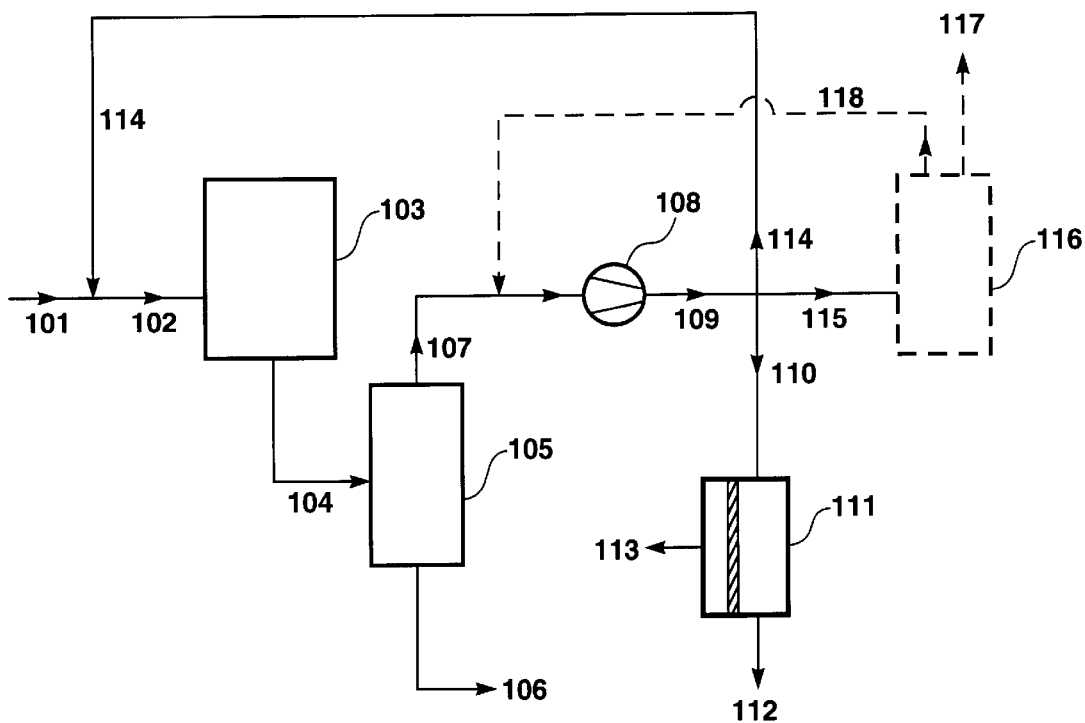
FIG. 1 is a schematic diagram of the basic embodiment of the invention.

The term stage-cut as used herein means the ratio of the membrane permeate volume flow to the membrane feed volume flow.

The term rubbery as used herein means rubbery or elastomeric.

The terms two-step and multi-step mean an arrangement of membrane modules or banks of modules connected together such that the residue stream from one module or bank of modules becomes the feedstream for the next.

The term two-stage and multi-stage mean an arrangement of membrane modules or banks of modules connected together such that the permeate stream from one module or bank of modules becomes the feedstream for the next.

The term membrane array means a set of membrane modules or banks of modules connected in a multi-step arrangement, a multi-stage arrangement, or mixtures or combinations of these.

The term product residue stream means the residue stream exiting a membrane array when the membrane separation process is complete. This stream may be derived from one membrane bank, or may be the pooled residue streams from several membrane banks.

The term product permeate stream means the permeate stream exiting a membrane array when the membrane separation process is complete. This stream may be derived from one membrane bank, or may be the pooled permeate streams from several membrane banks.

All percentages cited herein are by volume unless specifically stated otherwise.

In a basic embodiment, the process of the invention includes the following steps:
1. Performing one or more reaction steps in a reaction zone, at least one reaction step comprising a reaction of an organic feedstock and oxygen to make an organic product.
2. Treating the gas exiting the reactor to separate the organic product, and subsequently recovering the purified organic product.
3. Removing argon from the reaction zone recirculation loop.
4. Optionally removing carbon dioxide from the reaction zone recirculation loop.
5. Recirculating the unreacted feedstocks to the reaction zone.

In the process of the invention, steps 1 and 2, the reaction steps and organic product separation, can be carried out by any known techniques. Operation of selective oxidation reactors is well known in the art, as described in the Background section above.

The reactors themselves may be of any kind that provide for good contact between feedstocks and catalyst, and for good temperature control and removal of waste heat, such as shell-and-tube reactors, stirred tank reactors, and fluidized bed reactors. One or multiple reactors may be involved in the process, with the individual reactors carrying out the same or different unit operations. For example, acrylonitrile and phthalic anhydride are produced in simple single-stage oxidation reactions. However, phenol is manufactured in a two-step process. The first step is an oxidation reaction of cumene and sodium carbonate with oxygen in air to produce a cumene hydroperoxide. In the second step, a dilute acid is added to the crude hydroperoxide in a cleavage reactor, which produces phenol. Other types and/or combinations of reactors may be used, depending on the particular organic chemical product being manufactured.

The oxygen used in the reaction may be air, oxygen-enriched air, other oxygen-inert gas mixtures, or substantially pure oxygen. Although the discussion herein refers to oxygen-oxidation processes, reactors that use air as the oxidizing agent are also within the scope of the invention. More discussion of typical process configurations for air-oxidation reactors is included in parent application Ser. No. 08/890,856, now U.S. Pat. No. 5,817,841, which is incorporated herein by reference in its entirety.

The exact composition of the reaction mixture may be varied in conjunction with pressure, temperature and flow rate to provide a desired overall yield, efficiency per pass and so on, as is known in the art.

The reactions may be carried out at pressures up to 1,000 psia or above. However, many reactions may be effected at lower pressures, such as in the range 100–800 psia. Operating temperatures may be as high as 500° C., but, again, many reactions may be accomplished at lower temperatures, such as around 50–350° C.

Separation and recovery of the organic product from the raw gas exiting the reaction zone can be performed by any known method. For example, the raw gas can be passed into a scrubbing column and run counter-current to a water stream. Alternatively, the raw gas may be condensed and/or subjected to flash evaporation. The recovered liquid can then be passed to a purification train, including, for example, one or more stripping columns, distillation units, or rectifiers, such as are known in the art, for retrieval and purification of the organic product.

Steps 3 and 4, purging of argon and carbon dioxide from the reactor loop, represent an important aspect of the invention. In particular, the manner in which the argon purging is carried out differs from the prior art.

As was mentioned in the Background section above, current processes withdraw a stream of sufficient volume to maintain an acceptable argon concentration in the main recycle loop, and burn it as fuel or simply incinerate it. Since this stream often contains two or three times or more as much of the organic feedstock as argon, this means that 2–3 moles or more of organic may be lost for every mole of argon that is purged. The processes of the invention, on the other hand, are able to recover and recirculate significant amounts, typically 30% or more, such as 40%, 50%, 60%, 70%, 80%, 90%, 95% or even more of the organic content of this argon purge stream. That is, as a specific example, if the argon purge stream contains 3 moles of organic per mole of argon, use of the process of the invention can reduce the organic loss from 3 moles/mole of argon to 2.1 moles/mole of argon, 1.8 moles/mole of argon, 1.5 moles/mole of argon, 1.2 moles/mole of argon, 0.9 moles/mole of argon, 0.6 moles/mole of argon, 0.3 moles/mole of argon, 0.15 moles/mole of argon or even less.

Various process configurations for achieving this result are possible within the scope of the invention. FIGS. 1–6 show representative, but non-limiting, embodiments of the invention. It will be appreciated by those of skill in the art that these are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature-, level- and flow-measuring devices and the like.

Turning now to FIG. 1, stream 101, representing the raw materials needed to form the desired organic product, or to form an intermediate product used to form the organic product, is mixed with recirculating gas 114. Combined stream 102 is introduced into the reaction zone, 103, consisting of one or more reactors. Raw gas containing the newly formed organic product exits the reaction zone as stream 104, and passes to the separation and purification train, shown collectively as unit 105. The final organic product is withdrawn as stream 106.

The overhead stream 107 from the separation unit contains a mixture of organic feedstock, oxygen, carbon dioxide, nitrogen, argon, small amounts of hydrocarbons and trace amounts of other gases. The proportions of the component gases in the mix vary, depending on the specific reaction conditions. Stream 107 may be mixed with the carbon-dioxide-depleted stream 118, and the combined stream fed to compressor 108. Compressed stream 109 is typically split into three portions: stream 114, which is recirculated back to the reaction zone; stream 115, which is optionally subjected to a carbon dioxide removal treatment; and stream 110, which forms the feed to the argon removal unit.

It will be apparent to those of skill in the art that the relative sizes of stream 110, 114, and 115 are selected to maintain the desired concentration of carbon dioxide and argon in the reactor gas mix in accordance with plant specifications, and can be adjusted as necessary. As just one example, about half of compressed stream 109 might be recirculated directly, and the remaining half split about equally between the carbon dioxide purge system and the argon purge system. Typically, however, the feed stream, 110, to the argon removal system will be comparatively small, such as only 1%, 2%, 5% or 10% of stream 109.

Stream 115 is treated to remove excess carbon dioxide by any known method, depicted overall as unit 116 in the figure. Stream 118, depleted in carbon dioxide, is recirculated upstream of compressor 108. Carbon dioxide is vented via line 117.

In prior art processes, stream 110 would be purged. In the process of the invention, this stream is treated to remove excess argon. This is achieved by passing stream 110 across the feed side of membrane unit 111.

A synthetic polymer membrane separates the components of a gas or vapor mixture because the components permeate the membrane at different rates. The permeability, P [cm³ (STP)·cm/cm²·s·cmHg], of a polymer membrane material for a gas is defined as the rate at which that gas moves through a standard thickness [1 cm] of the material under a standard driving force [a pressure difference of 1 cmHg].

A measure of the ability of a membrane to separate two gases is the selectivity, $\alpha$, defined as the ratio of the gas permeabilities, $P_1/P_2$. The intrinsic selectivity of a polymer material is established by measuring the permeabilities with pure gas or vapor samples, then calculating the ratio. The actual selectivity obtained in a real separation process is established by making permeation measurements with gas mixtures. Selectivity can also be expressed as:

$$\alpha = \frac{D_1}{D_2} \cdot \frac{k_1}{k_2}$$

where D is the diffusion coefficient of the gas in the membrane [cm$^2$/s], which is a measure of the gas mobility, and k is the Henry's law sorption coefficient, which links the concentration of the gas in the membrane material to the pressure in the adjacent gas [cm$^3$(STP)/cm$^3$·cmHg], and is a measure of the gas solubility in the membrane material.

The ratio $D_1/D_2$ is the ratio of the diffusion coefficients of the two gases and can be viewed as the mobility selectivity, reflecting the different sizes of the two molecules. The ratio $k_1/k_2$ is the ratio of the Henry's law coefficients of the two gases and can be viewed as the solubility selectivity, reflecting the relative condensabilities of the two gases.

In all polymer materials, the diffusion coefficient decreases with increasing molecular size. Hence, the diffusion component of the selectivity always favors the passage of small molecules over large ones. The diffusion coefficient thus favors permeation of argon over organics. The solubility component of the selectivity, on the other hand, is a measure of the energy required for sorption and normally increases with molecular diameter, because larger molecules are normally more condensable than smaller ones. The solubility coefficient favors permeation of the organic over argon, therefore. The relative contribution of the diffusion and solubility coefficients determines the overall selectivity of a membrane material.

The balance between diffusion selectivity and solubility selectivity is different for glassy and rubbery polymers. In rubbery polymers, the solubility term is usually the dominant term, so that rubbery membranes are selective for larger, more condensable molecules over smaller, less condensable molecules. Furthermore, since the polymer chains in rubbery membranes are more flexible than in glassy membranes, the fluxes of all permeants, whether the more or less favored permeant, are generally higher through rubbery membranes than through glassy membranes.

In the case of separation of argon from an organic feedstock, such as ethylene, both components have fairly small molecules and both have very low boiling points and are not easily condensed. The smaller molecular size of argon means that glassy materials slightly favor the passage of argon over the organic. The relative condensability of the ethylene or other organic means that rubbery materials slightly favor the passage of the organic over argon. However, whether glassy or rubbery membrane materials are used to separate the components, the selectivity is relatively low. For example, polyimides and similar glassy materials have a selectivity for argon over ethylene of up to about 4, and silicone rubber and similar rubbery materials have a similar selectivity of about 4 for ethylene over argon. A selectivity of at least about 4 for the organic over argon is preferred for the process of the invention.

It might be supposed, therefore, that it is simply a matter of choice and convenience which type of membrane to use, and that essentially equivalent results will be obtained in either case. This, however, is not so, as we have shown. The difference in performance that can be achieved arises in part from the difference in stage-cuts needed to optimize the membrane separation, depending on whether the residue or the permeate stream is the vented stream. Stage-cut is defined as the ratio of total permeate flow to total feed flow, and is typically expressed as a percentage. For example, a stage-cut of 20% means that of 100 volumes of feed gas, 20 volumes pass to the permeate side and 80 volumes remain on the feed side.

When an organic-selective membrane is used, as is taught herein, the argon-enriched purge vent stream is the residue stream. In this case, at low stage-cuts, comparatively little removal of the organic from the feed stream will have been achieved, and if the residue stream is vented at this point, comparatively large amounts of organic will be lost. As the stage-cut increases, a higher proportion of the organic passes into the permeate stream, and the higher the stage-cut, the less organic will be left in the residue stream. Thus, recapture of any amount of organic feedstock is possible, at least theoretically, by an appropriately high choice of stage-cut. Of course, membrane area required to perform the separation scales in proportion to stage-cut, which will impose a practical limit on recovery.

Those of skill in the art will appreciate that the stage-cut used will vary with the specific feed composition, membrane performance and system operating conditions. As a guideline, it is preferred to operate at a stage-cut of at least about 30%, more preferably at least about 40%, and most preferably at least about 50%. It is expected that stage-cuts of 60%, 70% or even 80% or more may be used in some cases.

Returning to FIG. 1, membrane unit 111 contains organic-selective membranes, which generally means rubbery or elastomeric membranes. Examples of polymers that can be used to make elastomeric membranes, include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cispolyisoprene, poly(butene-1), polystyrene-butadiene copolymers, styrene/butadiene/styrene block copolymers, styrene/ethylene/butylene block copolymers, thermoplastic polyolefin elastomers, and block copolymers of polyethers, polyamides and polyesters. The preferred membrane material is silicone rubber, since silicone rubber membranes are already in commercial production and use for other separations.

As an alternative to a rubbery organic-selective membrane, organic-selective membranes can also be made from super-glassy materials, such as poly(trimethylsilylpropyne) [PTMSP] and the like, the general use of which is described in U.S. Pat. No. 5,281,255, for example. As yet another alternative, finely microporous inorganic membranes, such as the adsorbent carbon membranes described in U.S. Pat. No. 5,332,424, the pyrolysed carbon membranes described in U.S. Pat. No. 4,685,940, or certain ceramic membranes may be used. These alternatives, most of which exhibit acceptable organic selectivity only in the presence of a $C_{3+}$ hydrocarbon or other relatively condensable molecule in the gas mix, and most of which are less readily available than rubbery polymer membranes, are less preferred, but may be useful in some circumstances. Membranes comprising immobilized liquid films can also be used. However, these membranes tend to be unstable over long periods of time, and therefore are less preferred.

The membrane may take the form of a single homogeneous layer, an integral asymmetric membrane, a multilayer composite membrane, a membrane incorporating a gel or liquid layer or particulates, or any other form known in the art. Composite membranes, in which the elastomeric selective membrane layer is supported on a mechanically strong, highly permeable support layer, are preferred.

The membranes may be manufactured as flat sheets or as fibers and housed in any convenient module form, including spiral-wound modules, plate-and-frame modules and potted hollow-fiber modules. The making of all these types of membranes and modules is well known in the art. Flat-sheet membranes in spiral-wound modules are our most preferred choice.

Membrane unit 111 may contain a single membrane module or bank of modules or an array of modules. A single-stage membrane separation operation is adequate for many applications. If the residue stream requires further purification, it may be passed to a second bank of modules for a second processing step. If the permeate stream requires further concentration, it may be passed to a second bank of modules for a second-stage treatment. Such multistage or multistep processes, and variants thereof, will be familiar to those of skill in the art, who will appreciate that the membrane separation step may be configured in many possible ways, including single-stage, multistage, multistep, or more complicated arrays of two or more units in series or cascade arrangements. If an array of membranes is used, the stage-cut preferences cited above for obtaining good organic recovery refer to the overall stage-cut of the array. In other words, the stage-cut is the ratio of total product permeate stream flow to raw feed flow to the first membrane bank in the array.

A pressure difference between the feed and permeate sides of the membrane is used to provide a driving force for transmembrane permeation. Selective oxidation reactors are usually run at pressures in the range 100–800 psia, and the off-gas from the separation unit is recompressed to the required reactor pressure by compressor 108 for recirculation. Thus, it is normally possible, and is preferred, to operate the membrane system at the feed pressure available from the reactor recompressor without additional compression. If it is desired to increase the pressure difference across the membrane, this can be done by passing the membrane feed stream 110 through an additional compressor or by lowering the pressure on the permeate side by means of a vacuum pump, for example.

The membrane unit separates the feed stream 110 into permeate stream 113 and residue stream 112. The residue stream is vented from the process to any appropriate destination. For a typical stream, unless a very high stage-cut such as about 80% or above is used, the residue stream will be slightly enriched in hydrocarbon content compared with the membrane feed stream. Therefore, as in prior art processes, the stream may be incinerated or used as fuel. However, in the process of the invention, this will result in a much smaller loss of organic than was previously possible. By following the teachings given herein, it is possible to reduce the organic loss per mole of argon vented by as much as 50%, 60%, 70%, 80%, 90%, or even more.

Permeate stream 113, now depleted in argon and enriched in organic content, is withdrawn. The ultimate destination of the recovered organic is the main reaction zone. A number of options exist for the method of organic recycle, as discussed below and shown schematically in FIGS. 2–6.

Figure 2:
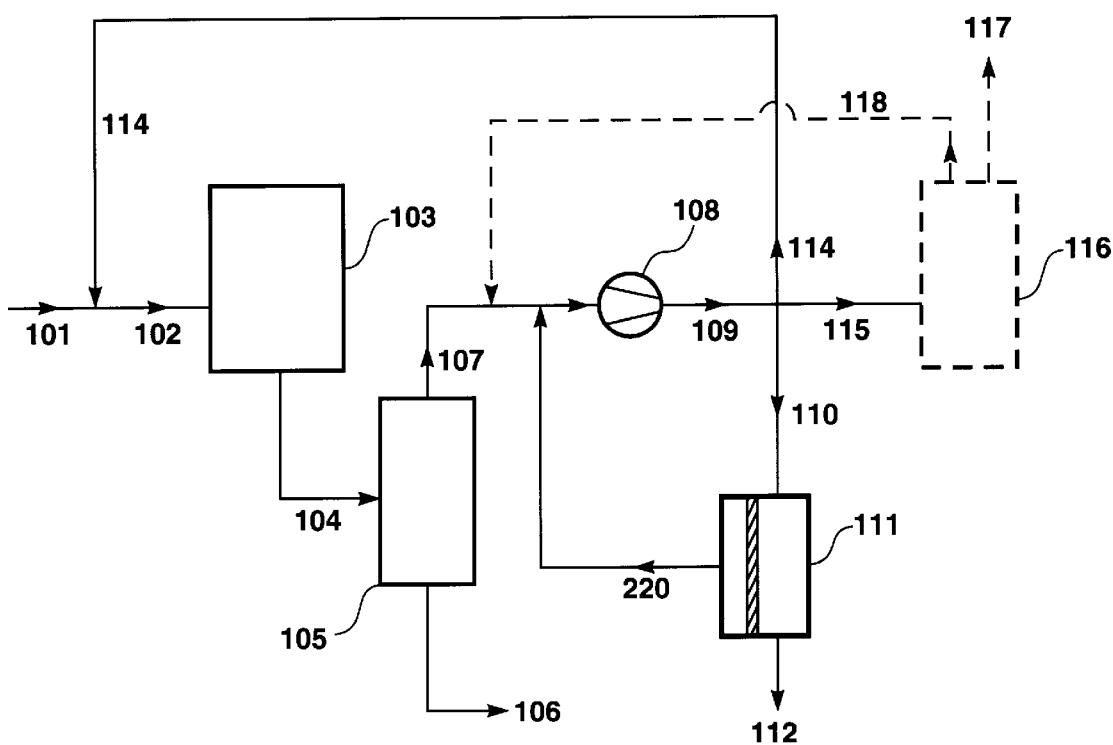
FIG. 2 is a schematic diagram of an alternative embodiment of the invention in which the membrane permeate is recycled to the main reactor loop.

One alternative embodiment is shown schematically in FIG. 2, in which like elements are numbered as in FIG. 1. In this figure, the permeate stream, 220, is returned to the main recycle loop by recirculating it upstream of compressor 108. This embodiment makes use of the excess horsepower from compressor 108, such as is often available, and thus involves no additional capital expense or maintenance.

Figure 3:
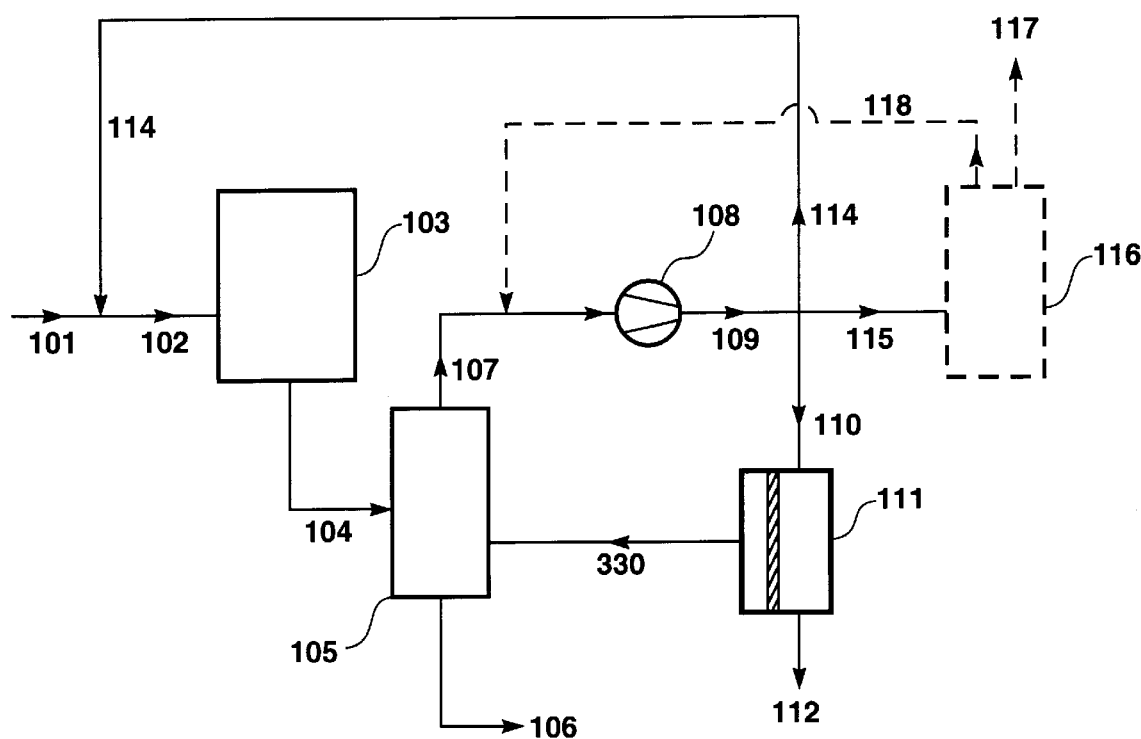
FIG. 3 is a schematic diagram of an alternative embodiment of the invention in which the membrane permeate is recycled to the separation and purification process loop.

Alternatively, the permeate can be returned to some point in the organic product separation and purification train, unit 105, as shown schematically in FIG. 3, in which like elements are numbered as in FIG. 1. FIG. 3 shows permeate stream 330 being passed directly to unit 105. The permeate could be added to, for example, a flash vessel, or to another unit in the train. Alternatively, the permeate could be added to a gaseous overhead stream from a unit upstream of a compressor that is typically present in the process loop. This embodiment also takes advantage of the excess horsepower available from an existing compressor in the process loop.

Figure 6:
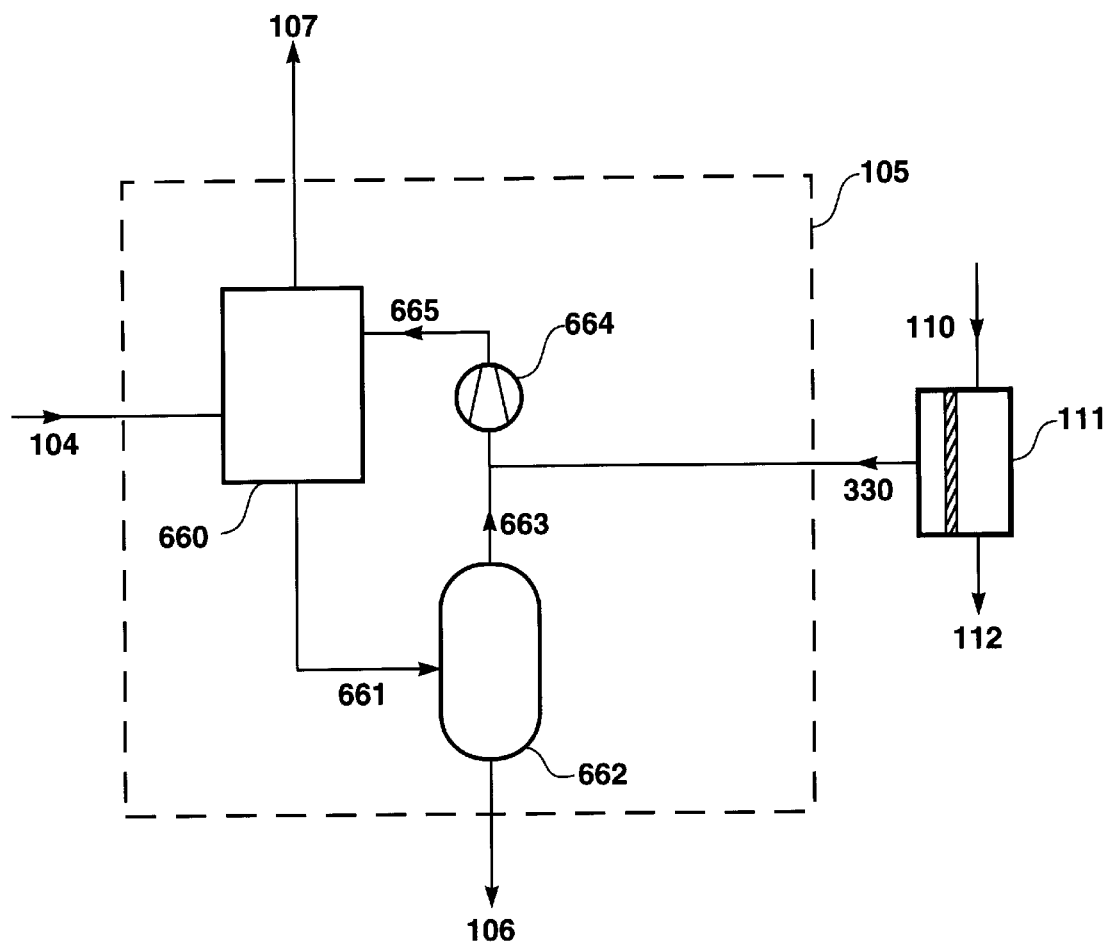
FIG. 6 is a schematic drawing of the an embodiment of the separation and purification process loop of FIG. 3 in more detail.

An example of the separation and purification train is shown in more detail in FIG. 6, in which like elements are numbered as in FIG. 3. In this figure, crude product stream 104 from the reaction zone enters a separation unit, 660, which may be any suitable separation method known in the art, such as a scrubber or condenser. The intermediate product, stream 661, is passed to purification unit 662, which may be one or more distillation units, stripping columns, flash vessels, or other purification techniques suitable for the particular organic product being manufactured.

As a specific example, phthalic anhydride is recovered and purified by removing the crude product, 104, from the reaction zone and passing it to condenser 660. Condensed product 661 passes to distillation column 662, from which is withdrawn pure phthalic anhydride as stream 106.

The gaseous overhead stream 663 is combined with the organic-feedstock-rich permeate stream 330 and recompressed in compressor 664. Compressed stream 665 is passed to unit 660 for further separation treatment. In this way, the permeate may be recirculated to the reaction zone using the excess horsepower available from an existing compressor in the process loop. Other examples of separation and purification combinations which may be useful in the manufacture of other organic chemical products include, but are not limited to, condensation followed by flash evaporation, scrubbing followed by stripping, and scrubbing followed by distillation.

Figure 4:
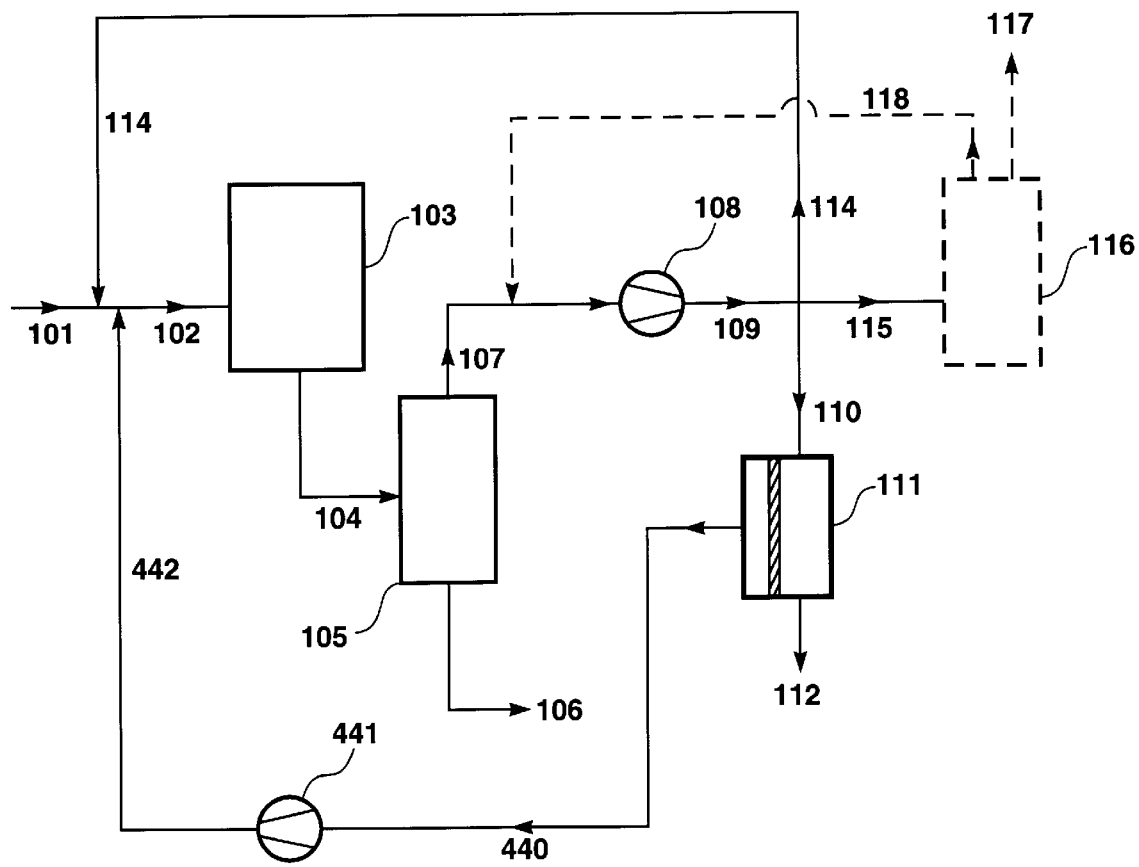
FIG. 4 is a schematic diagram of an alternative embodiment of the invention in which the membrane permeate is recycled directly to the reaction zone.

The permeate stream can also be recycled directly back to the reaction zone, as shown schematically in FIG. 4, in which like elements are numbered as in FIG. 1. Turning now to FIG. 4, permeate stream 440 is recompressed to the required reactor pressure in compressor 441. Compressed stream 442 joins with stream 101 along with recycle stream 114 to form combined reaction zone feed stream 102. This recycle method requires that an additional compressor be added to the existing plant, but can provide a large quantity of argon-depleted organic feedstock to be added directly to the reactor feed stream.

Figure 5:
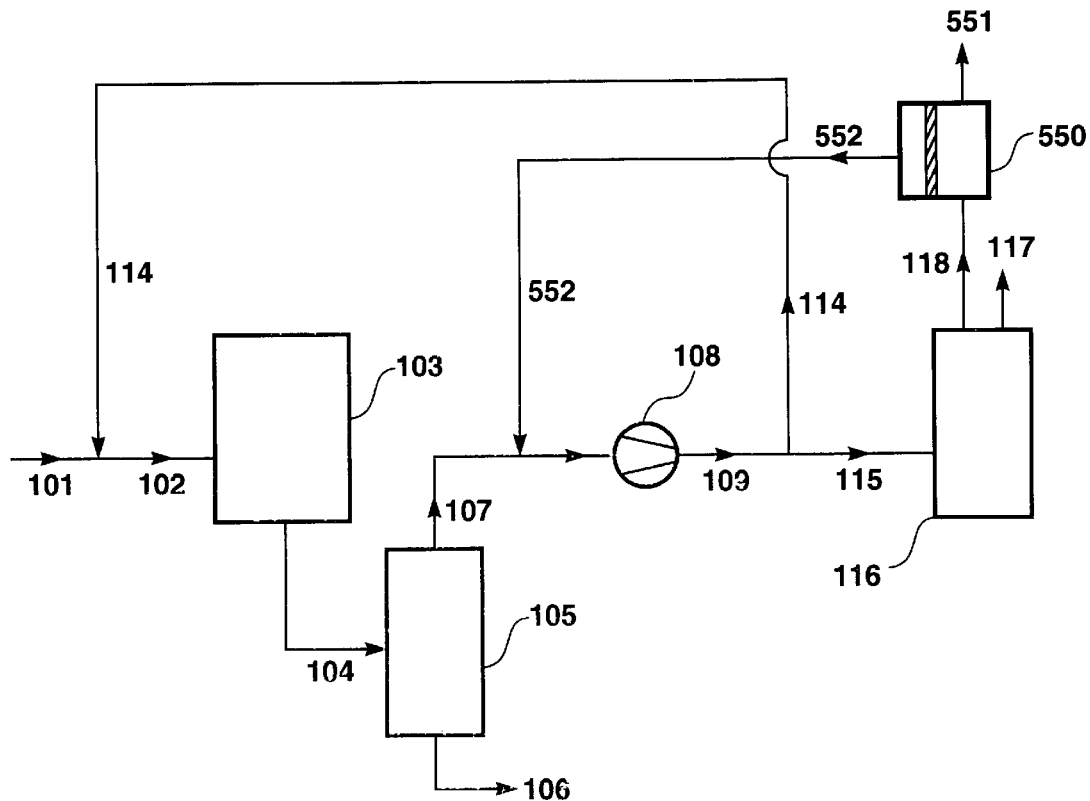
FIG. 5 is a schematic diagram of an alternative embodiment of the invention in which the carbon dioxide removal step and the argon removal step are carried out in series.

Yet another alternative embodiment, in which the carbon dioxide and argon removal operations are carried out in series, is shown schematically in FIG. 5, in which like elements are numbered as in FIG. 1. In FIG. 5, compressed overhead stream 109 is split into two portions, with one portion, stream 114, being recycled directly to the reactor feed stream. The other portion, stream 115, passes to carbon dioxide removal unit 116. Carbon-dioxide-depleted stream 118 exits the top of unit 116. This stream forms the feed to membrane unit 550. Organic-depleted residue stream 551 is discharged from the process to any appropriate destination. Permeate stream 552, enriched in organic and depleted in carbon dioxide and argon, is recycled upstream of compressor 108 for recirculation in the main reactor loop. Although the entirety of stream 118 is shown being passed to the membrane unit, it will be apparent to those of skill in the art that any fraction of stream 118 may be treated in the membrane unit, with the remainder of the stream being recycled to the reactor loop without argon-removal treatment. The amount of stream 118 to be passed to the membrane unit can be determined based on flow rates, efficiency per pass and so on, in accordance with plant specifications, and can be adjusted as necessary.

Based on the descriptions of FIGS. 1–6, those of skill in the art will appreciate that various other configurations are possible within the scope of the invention. As one example, stream 220 of FIG. 2 can be subjected to carbon dioxide removal treatment before recirculation. As another example, the argon removal membrane system can be positioned in series before the carbon dioxide removal treatment. That is, the apparatus arrangement shown in FIG. 5 can be reversed, so that membrane unit 550 is installed in line 115, or on a bypass line parallel to line 115, upstream of the carbon dioxide removal unit.

Thus, the scope of the invention is not limited to any specific configuration but to the use of an organic-selective membrane to provide improved argon-purging capability.

Similarly, although FIGS. 1 and 2 relate primarily to an oxygen-oxidation process, the process of the invention can also be carried out with air-oxidation reactors. In this case, the membrane system can be installed on the main vent from the purge absorber to recover nitrogen from the nitrogen purge stream, for example.

In another aspect, the invention is apparatus useful for manufacture of chemical intermediates. In this aspect, the invention includes the following elements:
(a) a reactor for reacting organic feedstock and oxygen;
(b) a product recovery unit connected to the reactor so that gas can pass from the reactor into the product recovery unit;
(c) an optional carbon dioxide removal unit connected to the product recovery unit;
(d) a membrane unit containing a membrane selectively permeable to organics over argon and connected to the product recovery unit;
(e) one or more lines for recirculating gases from the product recovery unit, the carbon dioxide removal unit and the membrane unit to the reactor.

As was discussed with regard to the process embodiments, many variations in the specific configuration are possible. For example, with reference to FIG. 2, 103 is the reactor; 105 forms the product recovery and purifcation unit; 116 forms the carbon dioxide removal unit; the membrane unit is 111; and lines 114, 118, and 220 are lines for recirculating gases.

With reference to FIG. 5, 103 is the reactor; 105 forms the product recovery and purification unit; 116 forms the carbon dioxide removal unit; the membrane unit is 550; and lines 114 and 552 are lines for recirculating gases. In this case, the connection of the membrane unit to the product recovery unit is indirect, through the carbon dioxide removal unit.

In yet another aspect, the invention is a process for treating an argon purge stream to vent argon and recapture organic feedstock in a chemical intermediate manufacturing process. In this aspect, the invention comprises:
(a) providing a membrane having a feed side and a permeate side, and being selectively permeable to the organic feedstock over argon;
(b) passing at least a portion of the purge stream across the feed side under conditions in which there is a pressure drop from the feed side to the permeate side;
(c) withdrawing from the feed side an argon-rich stream enriched in argon and depleted in organic compared with the purge stream;
(d) withdrawing from the permeate side an organic-rich permeate stream enriched in organic and depleted in argon compared with the purge stream;
(e) recirculating at least a portion of the organic-rich permeate stream to the chemical intermediate manufacturing process.

The invention is now illustrated in further detail by specific examples. These examples are intended to further clarify the invention, and are not intended to limit the scope in any way.

EXAMPLES

Example 1

Permeation Properties of Silicone Rubber Membrane Stamps

A microporous support membrane was dip-coated in a 6% dimethyl siloxane solution at 1 ft/min coating speed, then dried in an oven at 60° C. to crosslink the membrane. The resulting membranes had a nominal selective layer thickness of 2.7 $\mu$m. Samples of the finished composite membrane were cut into 12.6 cm$^2$ stamps and tested in a permeation test-cell apparatus with pure oxygen, nitrogen, argon, methane, ethylene, and carbon dioxide at 23° C. feed temperature, 50 psig feed pressure, and ambient permeate pressure. The gas fluxes of the membranes were measured, and the selectivities were calculated. The results of the tests are shown in Table 1. Any membrane with a selectivity less than the intrinsic selectivity of the material was considered defective.

TABLE 1

| Gas | Flux × 10$^{-6}$ cm$^3$(STP)/ cm$^2$ · sec · cmHg | Gas/Nitrogen Selectivity (−) |
|---|---|---|
| Nitrogen | 105 | — |
| Oxygen | 228 | 2.2 |
| Argon | 236 | 2.2 |
| Methane | 348 | 3.3 |
| Ethane | 800 | 7.6 |
| Ethylene | 983 | 9.4 |
| Carbon Dioxide | 1,360 | 13.0 |

Examples 2–5

Ethylene Recovery as a Function of Stage-Cut in a Vinyl Acetate Manufacturing Process

Example 2

A series of computer calculations were performed with a modeling program, ChemCad III (ChemStations, Inc., Houston, Tex.), to illustrate the effect of stage-cut on an ethylene/argon separation process using an ethylene-selective membrane.

The feed mixture was chosen to approximate a vent stream from a vinyl acetate recovery unit, and was assumed to contain the following components in the concentrations noted:

| | |
|---|---|
| 70% | Ethylene |
| 3% | Oxygen |
| 7% | Argon |
| 5% | Nitrogen |
| 13% | Carbon Dioxide |
| 1% | Methane |
| 1% | Ethane |

We assumed membrane pressure-normalized fluxes as follows, which were determined in Example 1 for silicone rubber membranes:

| | |
|---|---|
| Ethylene | 983 × 10$^{-6}$ cm$^3$(STP)/cm$^2$ · sec · cmHg |
| Oxygen | 228 × 10$^{-6}$ cm$^3$(STP)/cm$^2$ · sec · cmHg |
| Argon | 236 × 10$^{-6}$ cm$^3$(STP)/cm$^2$ · sec · cmHg |
| Nitrogen | 105 × 10$^{-6}$ cm$^3$(STP)/cm$^2$ · sec · cmHg |
| Carbon Dioxide | 1,360 × 10$^{-6}$ cm$^3$(STP)/cm$^2$ · sec · cmHg |

-continued

| | |
|---|---|
| Methane | 348 × 10⁻⁶ cm³(STP)/cm² · sec · cmHg |
| Ethane | 800 × 10⁻⁶ cm³(STP)/cm² · sec · cmHg |

We assumed the one-stage membrane separation operation as in FIG. 1. In this Figure, line 110 carries the compressed overhead stream from the vinyl acetate recovery unit to membrane unit 111. The ethylene-enriched permeate stream is withdrawn through line 113. The ethylene-depleted, argon-enriched residue stream is withdrawn through line 112.

The stage-cut was assumed to be about 60%. The results of the calculations are shown in Table 2.

TABLE 2

| Component/Parameter | Stream 110 | Stream 112 | Stream 113 |
|---|---|---|---|
| Mass Flow Rate (lb/h) | 517.6 | 210.6 | 307.1 |
| Flow Rate (scfm) | 100 | 40.7 | 59.2 |
| Temperature (° C.) | 25 | 21 | 21 |
| Pressure (psia) | 115 | 115 | 20 |
| Component (mol %) | | | |
| Ethylene | 70.0 | 60.1 | 76.8 |
| Oxygen | 3.0 | 5.5 | 1.3 |
| Argon | 7.0 | 12.8 | 3.0 |
| Nitrogen | 5.0 | 10.7 | 1.1 |
| Carbon Dioxide | 13.0 | 8.3 | 16.2 |
| Methane | 1.0 | 1.6 | 0.6 |
| Ethane | 1.0 | 1.0 | 1.0 |
| Component (lb/h) | | | |
| Ethylene | 328.2 | 114.8 | 213.4 |
| Argon | 46.7 | 34.7 | 12.0 |

Membrane Area: 7 m²

Example 3

Calculations were performed as in Example 2, except with a stage-cut of about 75%. The results of the calculations are shown in Table 3.

TABLE 3

| Component/Parameter | Stream 110 | Stream 112 | Stream 113 |
|---|---|---|---|
| Mass Flow Rate (lb/h) | 517.7 | 138.4 | 379.3 |
| Flow Rate (scfm) | 100 | 26.7 | 73.3 |
| Temperature (° C.) | 25 | 21 | 21 |
| Pressure (psia) | 115 | 115 | 20 |

TABLE 3-continued

| Component/Parameter | Stream 110 | Stream 112 | Stream 113 |
|---|---|---|---|
| Component (mol %) | | | |
| Ethylene | 70.0 | 52.1 | 76.5 |
| Oxygen | 3.0 | 7.2 | 1.5 |
| Argon | 7.0 | 16.5 | 3.5 |
| Nitrogen | 5.0 | 15.2 | 1.3 |
| Carbon Dioxide | 13.0 | 6.1 | 15.5 |
| Methane | 1.0 | 1.9 | 0.7 |
| Ethane | 1.0 | 1.0 | 1.0 |
| Component (lb/h) | | | |
| Ethylene | 328.2 | 65.1 | 263.1 |
| Argon | 46.7 | 29.4 | 17.3 |

Membrane Area: 9 m²

Example 4

Calculations were performed as in Example 2, except with a stage-cut of about 90%. The results of the calculation are shown in Table 4.

TABLE 4

| Component/Parameter | Stream 110 | Stream 112 | Stream 113 |
|---|---|---|---|
| Mass Flow Rate (lb/h) | 517.7 | 60.1 | 457.6 |
| Flow Rate (scfm) | 100 | 11.4 | 88.6 |
| Temperature (° C.) | 25 | 21 | 21 |
| Pressure (psia) | 115 | 115 | 20 |
| Component (mol %) | | | |
| Ethylene | 70.0 | 29.4 | 75.2 |
| Oxygen | 3.0 | 11.0 | 2.0 |
| Argon | 7.0 | 25.1 | 4.7 |
| Nitrogen | 5.0 | 29.0 | 1.9 |
| Carbon Dioxide | 13.0 | 2.4 | 14.4 |
| Methane | 1.0 | 2.4 | 0.8 |
| Ethane | 1.0 | 0.7 | 1.0 |
| Component (lb/h) | | | |
| Ethylene | 328.2 | 15.7 | 312.5 |
| Argon | 46.7 | 19.1 | 27.6 |

Membrane Area: 12 m²

Example 5

Table 5, compiled from Tables 2, 3, and 4, compares the ethylene losses and the ethylene recovery rates of the process of the invention at varying stage-cuts. As can be seen, the higher the stage-cut, the lower is the ethylene loss in the argon vent stream, and the greater is the ethylene recovery.

TABLE 5

| Parameter | No membrane | Table 2 | Table 3 | Table 4 |
|---|---|---|---|---|
| Stage-Cut (%) | — | 60 | 75 | 90 |
| Membrane Area (m²) | — | 7 | 9 | 12 |
| Ethylene concentration in vent stream (mol %) | 70.0 | 60.1 | 52.1 | 29.4 |
| Amount of Ethylene in vent stream (lb/h) | 328.2 | 114.8 | 65.1 | 15.7 |
| Moles of ethylene lost/mole of argon vented | 10 | 4.7 | 3.2 | 1.2 |
| Removal/Recovery compared to No membrane (%) | — | 65.0 | 80.2 | 95.2 |

Examples 6–9

Ethylene Recovery at Constant Level of Argon Purge in a Vinyl Acetate Manufacturing Process

Example 6

A series of computer calculations were performed with a modeling program, ChemCad III (ChemStations, Inc., Houston, Tex.), to illustrate the ethylene recovery that can be achieved when a constant level of argon removal is required.

The feed composition and membrane pressure-normalized fluxes were assumed to be as in Example 2. The stage-cut was assumed to be about 60%. Also as in Example 2, it was assumed that, absent the membrane recovery unit, the process vents about 47 lb of argon and 328 lb of ethylene per hour. The membrane process was configured to maintain this same argon purge rate. The results of the calculations are shown in Table 6.

TABLE 6

| Component/Parameter | Stream 110 | Stream 112 | Stream 113 |
| --- | --- | --- | --- |
| Mass Flow Rate (lb/h) | 698.8 | 284.3 | 414.5 |
| Flow Rate (scfm) | 135.0 | 55.0 | 80.0 |
| Temperature (° C.) | 25 | 21 | 21 |
| Pressure (psia) | 115 | 115 | 20 |
| Component (mol %) | | | |
| Ethylene | 70.0 | 60.1 | 76.8 |
| Oxygen | 3.0 | 5.5 | 1.3 |
| Argon | 7.0 | 12.8 | 3.0 |
| Nitrogen | 5.0 | 10.7 | 1.1 |
| Carbon Dioxide | 13.0 | 8.3 | 16.2 |
| Methane | 1.0 | 1.6 | 0.6 |
| Ethane | 1.0 | 1.0 | 1.0 |
| Component (lb/h) | | | |
| Ethylene | 443.0 | 155.0 | 288.0 |
| Argon | 63.0 | 46.8 | 16.2 |

Membrane Area: 9.4 m$^2$

The process vents 155 lb/h of ethylene compared to the no-membrane case in which 328 lb/h of ethylene was vented. Thus, a stage-cut of 60% yields an ethylene recovery of about 50%.

Example 7

Calculations were performed as in Example 6, except with a stage-cut of about 75%, again configuring the membrane process for venting about 47 lb/h of argon. The results of the calculations are shown in Table 7.

TABLE 7

| Component/Parameter | Stream 110 | Stream 112 | Stream 113 |
| --- | --- | --- | --- |
| Mass Flow Rate (lb/h) | 823.1 | 220.0 | 603.1 |
| Flow Rate (scfm) | 159.0 | 42.4 | 116.6 |
| Temperature (° C.) | 25 | 21 | 21 |
| Pressure (psia) | 115 | 115 | 20 |
| Component (mol %) | | | |
| Ethylene | 70.0 | 52.1 | 76.5 |
| Oxygen | 3.0 | 7.2 | 1.5 |
| Argon | 7.0 | 16.5 | 3.5 |
| Nitrogen | 5.0 | 15.2 | 1.3 |
| Carbon Dioxide | 13.0 | 6.1 | 15.5 |
| Methane | 1.0 | 1.9 | 0.7 |
| Ethane | 1.0 | 1.0 | 1.0 |
| Component (lb/h) | | | |
| Ethylene | 521.8 | 103.5 | 418.3 |
| Argon | 74.3 | 46.8 | 27.5 |

Membrane Area: 14.2 m$^2$

In this case, the process vents about 105 lb/h of ethylene compared to the no-membrane case in which 328 lb/h of ethylene was vented. In other words, the ethylene recovery is nearly 70%.

Example 8

Calculations were performed as in Example 6, except with a stage-cut of about 90%, again configuring the membrane process for venting about 47 lb/h of argon. The results of the calculations are shown in Table 8.

TABLE 8

| Component/Parameter | Stream 110 | Stream 112 | Stream 113 |
| --- | --- | --- | --- |
| Mass Flow Rate (lb/h) | 1,268.3 | 147.3 | 1,121 |
| Flow Rate (scfm) | 245 | 27.9 | 217.1 |
| Temperature (° C.) | 25 | 21 | 21 |
| Pressure (psia) | 115 | 115 | 20 |
| Component (mol %) | | | |
| Ethylene | 70.0 | 29.4 | 75.2 |
| Oxygen | 3.0 | 11.0 | 2.0 |
| Argon | 7.0 | 25.1 | 4.7 |
| Nitrogen | 5.0 | 29.0 | 1.9 |
| Carbon Dioxide | 13.0 | 2.4 | 14.4 |
| Methane | 1.0 | 2.4 | 0.8 |
| Ethane | 1.0 | 0.7 | 1.0 |
| Component (lb/h) | | | |
| Ethylene | 804.0 | 38.5 | 765.5 |
| Argon | 114.5 | 46.7 | 67.8 |

Membrane Area: 28.7 m$^2$

In this case, the process vents only about 40 lb/h of ethylene compared to the no-membrane case in which 328 lb/h of ethylene was vented. This represents an ethylene recovery of about 90%.

Example 9

Table 9, compiled from Tables 6, 7, and 8, compares the ethylene losses and the ethylene recovery rates of the process of the invention at varying stage-cuts. As can be seen, the higher the stage-cut, the lower is the ethylene loss in the argon vent stream, and the greater is the ethylene recovery, while still maintaining the 47-lb/h argon purge rate.

TABLE 9

| Parameter | No membrane | Table 6 | Table 7 | Table 8 |
|---|---|---|---|---|
| Stage-Cut (%) | — | 60 | 75 | 90 |
| Membrane Area (m$^2$) | — | 9.4 | 14.2 | 28.7 |
| Ethylene concentration in vent stream (mol %) | 70.0 | 60.1 | 52.1 | 29.4 |
| Amount of Ethylene in vent stream (lb/h) | 328.2 | 155.0 | 103.5 | 38.5 |
| Removal/Recovery compared to No membrane (%) | — | 52.8 | 68.5 | 88.3 |

The ethylene recovery rates shown in Table 9 are slightly lower than those shown in Table 5.

Examples 10–13

Ethylene Recovery as a Function of Stage-Cut in a Vinyl Acetate Manufacturing Process Example 10

A series of computer calculations were performed with a modeling program, ChemCad III (ChemStations, Inc., Houston, Tex.), as in Examples 2–5, to illustrate the effect of stage-cut on an ethylene/argon separation process using an ethylene-selective membrane.

In this set of calculations, the feed mixture was assumed to be leaner in ethylene and richer in carbon dioxide than in the previous examples, as noted below:

| | |
|---|---|
| 60% | Ethylene |
| 3% | Oxygen |
| 5% | Argon |
| 7% | Nitrogen |
| 20% | Carbon Dioxide |
| 2.5% | Methane |
| 2.5% | Ethane |

We assumed membrane pressure-normalized fluxes as follows, which were determined in Example 1 for silicone rubber membranes:

| | |
|---|---|
| Ethylene | 983 × 10$^{-6}$ cm$^3$(STP)/cm$^2$ · sec· cmHg |
| Oxygen | 228 × 10$^{-6}$ cm$^3$(STP)/cm$^2$ · sec· cmHg |
| Argon | 236 × 10$^{-6}$ cm$^3$(STP)/cm$^2$ · sec· cmHg |
| Nitrogen | 105 × 10$^{-6}$ cm$^3$(STP)/cm$^2$ · sec· cmHg |
| Carbon Dioxide | 1,360 × 10$^{-6}$ cm$^3$(STP)/cm$^2$ · sec· cmHg |
| Methane | 348 × 10$^{-6}$ cm$^3$(STP)/cm$^2$ · sec· cmHg |
| Ethane | 800 × 10$^{-6}$ cm$^3$(STP)/cm$^2$ · sec· cmHg |

We assumed the one-stage membrane separation operation as in FIG. 1. The stage-cut was assumed to be about 60%. The results of the calculations are shown in Table 10.

TABLE 10

| Component/Parameter | Stream 110 | Stream 112 | Stream 113 |
|---|---|---|---|
| Mass Flow Rate (lb/h) | 529.9 | 211.5 | 318.4 |
| Flow Rate (scfm) | 100 | 40.9 | 59.1 |
| Temperature (° C.) | 25 | 21 | 21 |
| Pressure (psia) | 115 | 115 | 20 |
| Component (mol %) | | | |
| Ethylene | 60.0 | 51.6 | 65.8 |
| Oxygen | 3.0 | 5.5 | 1.3 |
| Argon | 5.0 | 9.1 | 2.2 |
| Nitrogen | 7.0 | 14.9 | 1.5 |
| Carbon Dioxide | 20.0 | 12.8 | 25.0 |
| Methane | 2.5 | 4.0 | 1.5 |
| Ethane | 2.5 | 2.1 | 2.7 |
| Component (lb/h) | | | |
| Ethylene | 281.3 | 98.8 | 182.5 |
| Argon | 33.4 | 24.8 | 8.6 |

Membrane Area: 7 m$^2$

Example 11

Calculations were performed as in Example 10, except with a stage-cut of about 75%. The results of the calculations are shown in Table 11.

TABLE 11

| Component/Parameter | Stream 110 | Stream 112 | Stream 113 |
|---|---|---|---|
| Mass Flow Rate (lb/h) | 529.9 | 138.4 | 391.5 |
| Flow Rate (scfm) | 100 | 27.0 | 73.0 |
| Temperature (° C.) | 25 | 21 | 21 |
| Pressure (psia) | 115 | 115 | 20 |
| Component (mol %) | | | |
| Ethylene | 60.0 | 44.2 | 65.8 |
| Oxygen | 3.0 | 7.1 | 1.5 |
| Argon | 5.0 | 11.7 | 2.5 |
| Nitrogen | 7.0 | 21.0 | 1.8 |
| Carbon Dioxide | 20.0 | 9.4 | 23.9 |
| Methane | 2.5 | 4.8 | 1.7 |
| Ethane | 2.5 | 1.8 | 2.7 |
| Component (lb/h) | | | |
| Ethylene | 281.3 | 56.0 | 225.3 |
| Argon | 33.4 | 21.0 | 12.4 |

Membrane Area: 9 m$^2$

Example 12

Calculations were performed as in Example 10, except with a stage-cut of about 90%. The results of the calculations are shown in Table 12.

TABLE 12

| Component/Parameter | Stream 110 | Stream 112 | Stream 113 |
|---|---|---|---|
| Mass Flow Rate (lb/h) | 529.9 | 61.7 | 468.2 |
| Flow Rate (scfm) | 100 | 12.2 | 87.8 |
| Temperature (° C.) | 25 | 21 | 21 |
| Pressure (psia) | 115 | 115 | 20 |

TABLE 12-continued

| Component/Parameter | Stream 110 | Stream 112 | Stream 113 |
|---|---|---|---|
| Component (mol %) | | | |
| Ethylene | 60.0 | 24.3 | 64.9 |
| Oxygen | 3.0 | 10.4 | 2.0 |
| Argon | 5.0 | 16.8 | 3.4 |
| Nitrogen | 7.0 | 38.0 | 2.7 |
| Carbon Dioxide | 20.0 | 3.7 | 22.3 |
| Methane | 2.5 | 5.8 | 2.0 |
| Ethane | 2.5 | 1.0 | 2.7 |
| Component (lb/h) | | | |
| Ethylene | 281.3 | 13.9 | 267.4 |
| Argon | 33.4 | 13.7 | 19.7 |

Membrane Area: 12 m$^2$

Example 13

Table 13, compiled from information in Tables 10, 11, and 12, compares the ethylene losses and the ethylene recovery rates of the process of the invention at varying stage-cuts. As can be seen, the higher the stage-cut, the lower is the ethylene loss in the argon vent stream, and the greater is the ethylene recovery.

TABLE 13

| Parameter | No membrane | Table 10 | Table 11 | Table 12 |
|---|---|---|---|---|
| Stage-Cut (%) | — | 60 | 75 | 90 |
| Membrane Area (m$^2$) | — | 7 | 9 | 12 |
| Ethylene concentration in vent stream (mol %) | 60.0 | 51.6 | 44.2 | 24.3 |
| Amount of Ethylene in vent stream (lb/h) | 281.3 | 98.8 | 56.0 | 13.9 |
| Moles of ethylene lost/mole of argon vented | 12 | 4.0 | 2.7 | 1.0 |
| Removal/Recovery compared to No membrane (%) | — | 64.9 | 80.1 | 95.1 |

Examples 14–17

Ethylene Recovery at Constant Level of Argon Purge in a Vinyl Acetate Manufacturing Process

Example 14

A series of computer calculations were performed with a modeling program, ChemCad III (ChemStations, Inc., Houston, Tex.), to illustrate the ethylene recovery that can be achieved when a constant level of argon removal is required. The feed composition and membrane pressure-normalized fluxes were assumed to be as in Example 10. The stage-cut was assumed to be about 60%. Also as in Example 10, it was assumed that, absent the membrane recovery unit, the process vents about 33 lb of argon and 281 lb of ethylene per hour. The membrane process was configured to maintain this same argon purge rate. The results of the calculations are shown in Table 14.

TABLE 14

| Component/Parameter | Stream 110 | Stream 112 | Stream 113 |
|---|---|---|---|
| Mass Flow Rate (lb/h) | 713.2 | 284.7 | 428.5 |
| FlowRate (scfm) | 134.6 | 55.0 | 79.6 |
| Temperature (° C.) | 25 | 21 | 21 |

TABLE 14-continued

| Component/Parameter | Stream 110 | Stream 112 | Stream 113 |
|---|---|---|---|
| Pressure (psia) | 115 | 115 | 20 |
| Component (mol %) | | | |
| Ethylene | 60.0 | 51.6 | 65.8 |
| Oxygen | 3.0 | 5.5 | 1.3 |
| Argon | 5.0 | 9.1 | 2.2 |
| Nitrogen | 7.0 | 14.9 | 1.5 |
| Carbon Dioxide | 20.0 | 12.8 | 25.0 |
| Methane | 2.5 | 4.0 | 1.5 |
| Ethane | 2.5 | 2.1 | 2.7 |
| Component (lb/h) | | | |
| Ethylene | 378.6 | 133.0 | 245.6 |
| Argon | 44.9 | 33.4 | 11.5 |

Membrane Area: 9 m$^2$

The process vents 133 lb/h of ethylene compared to the no-membrane case in which 281 lb/h of ethylene was vented. Thus, a stage-cut of 60% yields an ethylene recovery of about 50%.

Example 15

Calculations were performed as in Example 14, except with a stage-cut of 75%. The results of the calculations are shown in Table 15.

TABLE 15

| Component/Parameter | Stream 110 | Stream 112 | Stream 113 |
|---|---|---|---|
| Mass Flow Rate (lb/h) | 841.4 | 219.7 | 621.7 |
| Flow Rate (scfm) | 158.8 | 42.9 | 115.9 |
| Temperature (° C.) | 25 | 21 | 21 |
| Pressure (psia) | 115 | 115 | 20 |
| Component (mol %) | | | |
| Ethylene | 60.0 | 44.2 | 65.8 |
| Oxygen | 3.0 | 7.1 | 1.5 |
| Argon | 5.0 | 11.7 | 2.5 |
| Nitrogen | 7.0 | 21.0 | 1.8 |
| Carbon Dioxide | 20.0 | 9.4 | 23.9 |
| Methane | 2.5 | 4.8 | 1.7 |
| Ethane | 2.5 | 1.8 | 2.7 |
| Component (lb/h) | | | |
| Ethylene | 446.7 | 88.9 | 357.8 |
| Argon | 53.0 | 33.4 | 19.6 |

Membrane Area: 14 m$^2$

In this case, the process vents about 90 lb/h of ethylene compared to the no-membrane case in which 281 lb/h of ethylene was vented. In other words, the ethylene recovery is nearly 70%.

Example 16

Calculations were performed as in Example 14, except with a stage-cut of 90%. The results of the calculations are shown in Table 16.

TABLE 16

| Component/Parameter | Stream 110 | Stream 112 | Stream 113 |
|---|---|---|---|
| Mass Flow Rate (lb/h) | 1,295.5 | 150.8 | 1,144.7 |
| Flow Rate (scfm) | 244.5 | 29.7 | 214.8 |
| Temperature (° C.) | 25 | 21 | 21 |
| Pressure (psia) | 115 | 115 | 20 |
| Component (mol %) | | | |
| Ethylene | 60.0 | 24.3 | 64.9 |
| Oxygen | 3.0 | 10.4 | 2.0 |
| Argon | 5.0 | 16.8 | 3.4 |
| Nitrogen | 7.0 | 38.0 | 2.7 |
| Carbon Dioxide | 20.0 | 3.7 | 22.3 |
| Methane | 2.5 | 5.8 | 2.0 |
| Ethane | 2.5 | 1.0 | 2.7 |
| Component (lb/h) | | | |
| Ethylene | 687.8 | 33.9 | 653.9 |
| Argon | 81.6 | 33.4 | 48.2 |

Membrane Area: 29 m$^2$

In this case, the process vents only about 33 lb/h of ethylene compared to the no-membrane case in which 281 lb/h of ethylene was vented. This represents an ethylene recovery of about 90%.

Example 17

Table 17, compiled from Tables 14, 15, and 16, compares the ethylene losses and the ethylene recovery rates of the process of the invention at varying stage-cuts. As can be seen, the higher the stage-cut, the lower is the ethylene loss in the argon vent stream, and the greater is the ethylene recovery, while still maintaining the 33-lb/h argon purge rate.

TABLE 17

| Parameter | No membrane | Table 14 | Table 15 | Table 16 |
|---|---|---|---|---|
| Stage-Cut (%) | — | 60 | 75 | 90 |
| Membrane Area (m$^2$) | — | 9 | 14 | 29 |
| Ethylene concentration in vent stream (mol %) | 60.0 | 51.2 | 44.2 | 24.3 |
| Amount of Ethylene in vent stream (lb/h) | 281.3 | 133.0 | 88.9 | 33.9 |
| Removal/Recovery compared to No membrane (%) | — | 52.7 | 68.4 | 87.9 |

The elthylene recovery rates shown in Table 17 are slightly lower than those shown in Table 13.

Examples 18–25

Ethylene/Argon Separation According to the Process of the Invention

Example 18

A series of computer calculations were performed with a computer modeling program, ChemCad III (ChemStations, Inc. Houston, Tex.) to illustrate the effect of various stage-cuts on an ethylene/argon separation process according to the process of the invention using an ethylene-selective membrane. For simplicity, the feed stream was assumed to have only three components: 30% ethylene, 10% argon, and 60% methane, approximating the composition of the gas from an ethylene oxide reactor after carbon dioxide and ethylene oxide removal. We assumed membrane pressure-normalized fluxes as follows, as are typical of rubbery membranes:

| Ethylene | $100 \times 10^{-6}$ cm$^3$(STP)/cm$^2$.sec.cmHg |
|---|---|
| Argon | $25 \times 10^{-6}$ cm$^3$(STP)/cm$^2$.sec.cmHg |
| Methane | $35 \times 10^{-6}$ cm$^3$(STP)/cm$^2$.sec.cmHg |

We assumed a one-stage separation as in FIG. 1. The permeate stream withdrawn through line 113 contains mostly ethylene and methane. Most of the argon, along with some ethylene and methane, is withdrawn as a residue stream through line 112. The stage-cut was assumed to be 37%. The results of the calculations are shown in Table 18.

TABLE 18

| Component/Parameter | Stream 110 | Stream 112 | Stream 113 |
|---|---|---|---|
| Mass Flow Rate (lb/h) | 368.3 | 224.7 | 143.5 |
| Flow Rate (scfm) | 100 | 62.8 | 37.2 |
| Temperature (° C.) | 227 | 226 | 226 |
| Pressure (psia) | 200 | 200 | 20 |
| Component (mol %) | | | |
| Ethylene | 30.0 | 20.0 | 46.9 |
| Argon | 10.0 | 12.4 | 6.0 |
| Methane | 60.0 | 67.6 | 47.1 |

Membrane Area: 39 m$^2$

Example 19

A computer calculation was performed as in Example 18, except the stage-cut was assumed to be 66%. The results of the calculations are shown in Table 19.

TABLE 19

| Component/Parameter | Stream 110 | Stream 112 | Stream 113 |
|---|---|---|---|
| Mass Flow Rate (lb/h) | 368.3 | 118.5 | 249.8 |
| Flow Rate (scfm) | 100 | 33.8 | 66.2 |
| Temperature (° C.) | 227 | 225 | 225 |
| Pressure (psia) | 200 | 200 | 20 |
| Component (mol %) | | | |
| Ethylene | 30.0 | 10.0 | 40.2 |
| Argon | 10.0 | 15.7 | 7.1 |
| Methane | 60.0 | 74.3 | 52.7 |

Membrane Area: 74 m$^2$

Example 20

A computer calculation was performed as in Example 18, except the stage-cut was assumed to be 80%. The results of the calculations are shown in Table 20.

TABLE 20

| Component/Parameter | Stream 110 | Stream 112 | Stream 113 |
|---|---|---|---|
| Mass Flow Rate (lb/h) | 368.3 | 70.5 | 297.8 |
| Flow Rate (scfm) | 100 | 20.0 | 80.0 |
| Temperature (° C.) | 227 | 225 | 225 |
| Pressure (psia) | 200 | 200 | 20 |
| Component (mol %) | | | |
| Ethylene | 30.0 | 5.0 | 36.3 |
| Argon | 10.0 | 18.4 | 7.9 |
| Methane | 60.0 | 76.6 | 55.8 |

Membrane Area: 92 m$^2$

Example 21

A computer calculation was performed as in Example 18, except the stage-cut was assumed to be 86%. The results of the calculations are shown in Table 21.

TABLE 21

| Component/Parameter | Stream 110 | Stream 112 | Stream 113 |
|---|---|---|---|
| Mass Flow Rate (lb/h) | 368.3 | 49.8 | 318.4 |
| Flow Rate (scfm) | 100 | 14.0 | 86.0 |
| Temperature (° C.) | 227 | 225 | 225 |
| Pressure (psia) | 200 | 200 | 20 |
| Component (mol %) | | | |
| Ethylene | 30.0 | 3.0 | 34.4 |
| Argon | 10.0 | 20.3 | 8.3 |
| Methane | 60.0 | 76.7 | 57.3 |

Membrane Area: 101 m$^2$

Example 22

A computer calculation was performed as in Example 18, except the stage-cut was assumed to be 89%. The results of the calculations are shown in Table 22.

TABLE 22

| Component/Parameter | Stream 110 | Stream 112 | Stream 113 |
|---|---|---|---|
| Mass Flow Rate (lb/h) | 368.3 | 38.4 | 329.9 |
| Flow Rate (scfm) | 100 | 10.7 | 89.3 |
| Temperature (° C.) | 227 | 225 | 225 |
| Pressure (psia) | 200 | 200 | 20 |
| Component (mol %) | | | |
| Ethylene | 30.0 | 2.0 | 33.3 |
| Argon | 10.0 | 21.7 | 8.6 |
| Methane | 60.0 | 76.3 | 58.1 |

Membrane Area: 106 m$^2$

Example 23

A computer calculation was performed as in Example 18, except the stage-cut was assumed to be 93%. The results of the calculations are shown in Table 23.

TABLE 23

| Component/Parameter | Stream 110 | Stream 112 | Stream 113 |
|---|---|---|---|
| Mass Flow Rate (lb/h) | 368.3 | 24.9 | 343.4 |
| Flow Rate (scfm) | 100 | 6.8 | 93.2 |
| Temperature (° C.) | 227 | 225 | 225 |
| Pressure (psia) | 200 | 200 | 20 |
| Component (mol %) | | | |
| Ethylene | 30.0 | 1.0 | 32.1 |
| Argon | 10.0 | 24.2 | 9.0 |
| Methane | 60.0 | 74.8 | 58.9 |

Membrane Area: 112 m$^2$

Example 24

A computer calculation was performed as in Example 18 except the stage-cut was assumed to be 96%. The results of the calculations are shown in Table 24.

TABLE 24

| Component/Parameter | Stream 110 | Stream 112 | Stream 113 |
|---|---|---|---|
| Mass Flow Rate (lb/h) | 368.3 | 16.4 | 351.9 |
| Flow Rate (scfm) | 100 | 4.4 | 95.6 |
| Temperature (° C.) | 227 | 225 | 225 |
| Pressure (psia) | 200 | 200 | 20 |
| Component (mol %) | | | |
| Ethylene | 30.0 | 0.5 | 31.3 |
| Argon | 10.0 | 26.6 | 9.2 |
| Methane | 60.0 | 72.9 | 59.4 |

Membrane Area: 115 m$^2$

Example 25

Comparison of Vent Stream Concentrations as a Function of Stage-Cut

Figure 7:
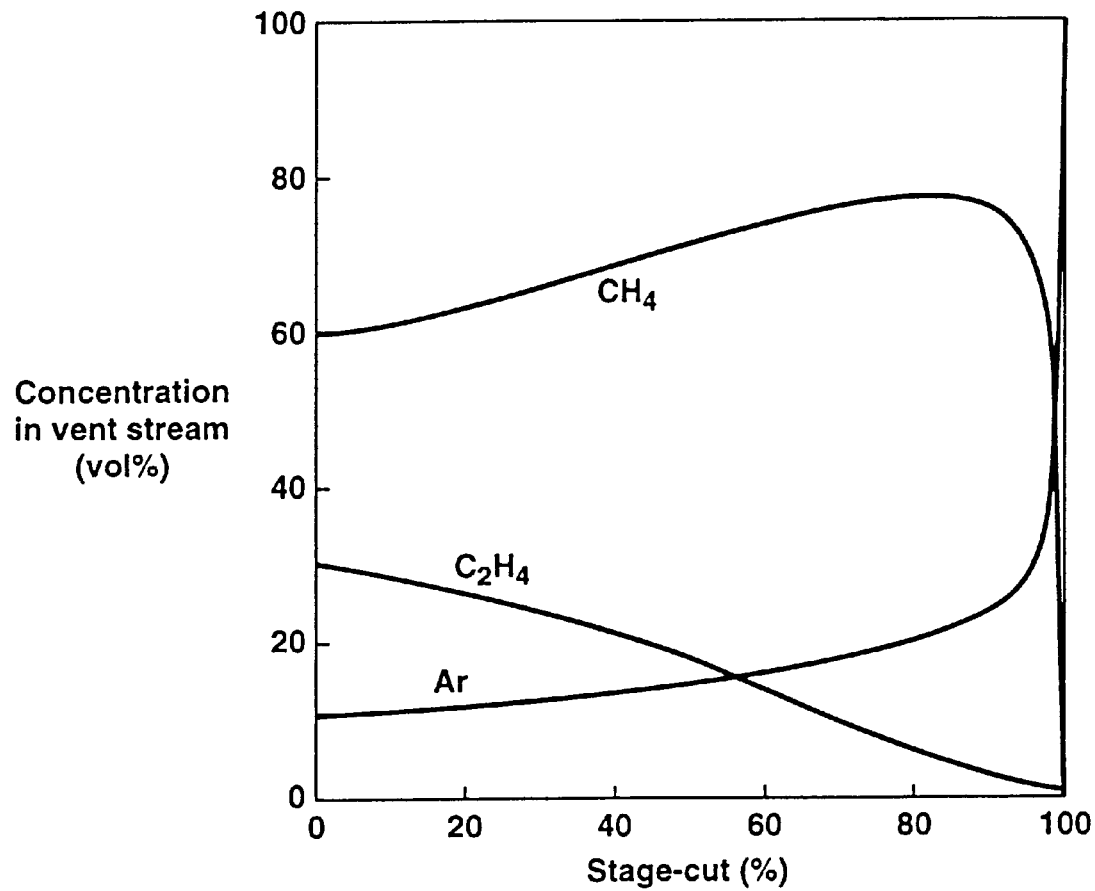
FIG. 7 is a graph showing the relationship between membrane stage-cut and component concentration in the vent stream from the membrane for an ethylene-selective membrane.

FIG. 7 is a graph showing the concentrations of methane, ethylene and argon in the vent stream as a function of stage-cut, according to the calculations in Examples 18–24 can be seen, the higher stage-cuts yielded the highest argon concentration and the lowest ethylene concentration in the vent (residue) stream. Thus, to obtain the highest ethylene recovery in the product (permeate) stream, it is desirable to operate the process at the highest stage-cut possible. At stage-cuts above about 85%, ethylene losses can be almost eliminated. Thus, there is no inherent limit on ethylene recovery.

Example 26

FIG. 7 was used to interpolate the ethylene loss and ethylene recovery that can be obtained at various stage-cuts with the process of the invention. The results of the calculations are shown in Table 25. The ethylene loss was expressed as the ratio of moles of ethylene in the vent (residue) stream to moles of argon in the vent stream. The methane loss was likewise expressed as the ratio of moles of methane in the vent stream to moles of argon in the vent stream. The ethylene recovery was defined as the difference in ethylene loss with and without the membrane recovery process, expressed as a percentage of the ethylene loss without the membrane recovery process. For example, since the feed composition is 300% ethylene, 10% argon, and 60% methane, if no membrane recovery step is in place, the purging operation would release 3 moles of ethylene for every 1 mole of argon released. In the 60% stage-cut case, 13/15 (0.87) moles of ethylene are released for every mole of argon released. Thus the ethylene recovery provided by the membrane step is (3−0.87)=2.13 moles, or 2.13/3=71% recovery compared with the "no-membrane" case.

TABLE 25

| Stage-Cut | Concentration in Vent Stream (mol %) | | | Ethylene Loss (moles/mole argon) | Methane Loss (moles/mole argon) | Ethylene Recovery |
|---|---|---|---|---|---|---|
| (%) | Argon | Ethylene | Methane | | | (%) |
| 90 | 23 | 2 | 76 | 0.09 | 3.3 | 97 |
| 80 | 19 | 5 | 77 | 0.26 | 4.1 | 91 |
| 70 | 16 | 9 | 75 | 0.56 | 4.7 | 81 |
| 60 | 15 | 13 | 73 | 0.87 | 4.9 | 71 |

Examples 27–30

Ethylene-Permeable-Membrane Process on a Multi-Component Stream

Example 27

Calculations were performed as in Example 18, to determine the separation that can be achieved by a one-stage membrane process as in FIG. 1. The feed mixture was chosen to be more closely representative of an actual vent stream from an ethylene oxide reactor, and was assumed to contain the following components in the concentrations noted:

| | |
|---|---|
| 28% | Ethylene |
| 6% | Oxygen |
| 3.5% | Carbon Dioxide |
| 2% | Nitrogen |
| 10% | Argon |
| 50.5% | Methane |

We assumed membrane pressure-normalized fluxes as follows, which were determined in Example 1 for silicone rubber membranes:

| | |
|---|---|
| Ethylene | 983 × 10$^{-6}$ cm$^3$(STP)/cm$^2$.sec.cmHg |
| Oxygen | 228 × 10$^{-6}$ cm$^3$(STP)/cm$^2$.sec.cmHg |
| Carbon Dioxide | 1,360 × 10$^{-6}$ cm$^3$(STP)/cm$^2$.sec.cmHg |
| Nitrogen | 105 × 10$^{-6}$ cm$^3$(STP)/cm$^2$.sec.cmHg |
| Argon | 236 × 10$^{-6}$ cm$^3$(STP)/cm$^2$.sec.cmHg |
| Methane | 348 × 10$^{-6}$ cm$^3$(STP)/cm$^2$.sec.cmHg |

The stage-cut was set at 80.3%. The results of the calculation are shown in Table 26.

TABLE 26

| Component/Parameter | Stream 110 | Stream 112 | Stream 113 |
|---|---|---|---|
| Mass Flow Rate (lb/h) | 400.6 | 77.5 | 323.1 |
| Flow Rate (scfm) | 100 | 19.7 | 80.3 |
| Temperature (° C.) | 207 | 205 | 205 |
| Pressure (psia) | 200 | 200 | 20 |
| Component (mol %) | | | |
| Ethylene | 28.0 | 4.0 | 33.9 |
| Oxygen | 6.0 | 11.4 | 4.7 |
| Carbon Dioxide | 3.5 | 0.2 | 4.3 |
| Nitrogen | 2.0 | 6.4 | 0.9 |
| Argon | 10.0 | 18.4 | 7.9 |
| Methane | 50.5 | 59.7 | 48.2 |

Membrane Area: 10 m$^2$

Table 27 shows the ethylene loss that occurs when the parameters in Table 26 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 27

| Component | Ethylene | Oxygen | Carbon Dioxide | Nitrogen | Argon | Methane |
|---|---|---|---|---|---|---|
| Concentration in vent stream (mol %) | 4.0 | 11.4 | 0.2 | 6.4 | 18.4 | 59.7 |
| Moles lost/mole of argon vented | 0.22 | 0.62 | 0.01 | 0.35 | 1.0 | 3.24 |
| Moles lost/mole of argon vented (No membrane) | 2.8 | 0.6 | 0.35 | 0.2 | 1.0 | 5.05 |
| Removal/Recovery compared to No membrane (%) | 92.1 | (3.3) | 97.1 | (75) | — | 35.8 |

Membrane Area: 26.9 m$^2$
Theoretical Horsepower: 38.7

Example 28

Calculations were performed as in Example 27, except with a stage-cut of 87%. The results of the calculations are shown in Table 28.

TABLE 28

| Component/Parameter | Stream 110 | Stream 112 | Stream 113 |
|---|---|---|---|
| Mass Flow Rate (lb/h) | 400.6 | 52.2 | 348.4 |
| Flow Rate (scfm) | 100 | 13.0 | 87.0 |
| Temperature (° C.) | 233 | 231 | 231 |
| Pressure (psia) | 200 | 200 | 20 |
| Component (mol %) | | | |
| Ethylene | 28.0 | 2.0 | 31.9 |
| Oxygen | 6.0 | 12.6 | 5.0 |
| Carbon Dioxide | 3.5 | 0.07 | 4.0 |
| Nitrogen | 2.0 | 8.3 | 1.1 |
| Argon | 10.0 | 20.1 | 8.5 |
| Methane | 50.5 | 56.9 | 49.5 |

Membrane Area: 11 m²

Table 29 shows the ethylene loss that occurs when the parameters in Table 28 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 29

| Component | Ethylene | Oxygen | Carbon Dioxide | Nitrogen | Argon | Methane |
|---|---|---|---|---|---|---|
| Concentration in vent stream (mol %) | 2.0 | 12.6 | 0.07 | 8.3 | 20.1 | 56.9 |
| Moles lost/mole of argon vented | 0.10 | 0.63 | 0.003 | 0.41 | 1.0 | 2.83 |
| Moles lost/mole of argon vented (No membrane) | 2.8 | 0.6 | 0.35 | 0.2 | 1.0 | 5.05 |
| Removal/Recovery compared to No membrane (%) | 96.4 | (5) | 99 | (105) | — | 44.0 |

Membrane Area: 41.7 m²
Theoretical Horsepower: 69.5

Example 29

Calculations were performed as in Example 27, except with a stage-cut of 91.2%. The results of the calculation are shown in Table 30.

TABLE 30

| Component/Parameter | Stream 110 | Stream 112 | Stream 113 |
|---|---|---|---|
| Mass Flow Rate (lb/h) | 400.6 | 36.2 | 364.4 |
| Flow Rate (scfm) | 100 | 8.8 | 91.2 |
| Temperature (° C.) | 233 | 231 | 231 |
| Pressure (psia) | 200 | 200 | 20 |
| Component (mol %) | | | |
| Ethylene | 28.0 | 1.0 | 30.6 |
| Oxygen | 6.0 | 13.6 | 5.3 |
| Carbon Dioxide | 3.5 | 0.03 | 3.8 |
| Nitrogen | 2.0 | 10.6 | 1.2 |
| Argon | 10.0 | 21.6 | 8.9 |
| Methane | 50.5 | 53.2 | 50.2 |

Membrane Area: 12 m²

Table 31 shows the ethylene loss that occurs when the parameters in Table 30 are used. Also shown is the improvement in ethylene recovery compared to a reactor that does not use a membrane process to treat the vent stream. A normalizing factor was applied to the membrane area, so that in all cases the removal/recovery calculations could be compared on the basis of a vent stream that will release 10 scfm of argon.

TABLE 31

| Component | Ethylene | Oxygen | Carbon Dioxide | Nitrogen | Argon | Methane |
|---|---|---|---|---|---|---|
| Concentration in vent stream (mol %) | 1.0 | 13.6 | 0.03 | 10.6 | 21.6 | 53.2 |
| Moles lost/mole of argon vented | 0.05 | 0.63 | 0.001 | 0.49 | 1.0 | 2.46 |
| Moles lost/mole of argon vented (No membrane) | 2.8 | 0.6 | 0.35 | 0.2 | 1.0 | 5.05 |
| Removal/Recovery compared to No membrane (%) | 98.2 | (5) | 99.7 | (145) | — | 51.3 |

Membrane Area: 61.4 m²
Theoretical Horsepower: 100.3

Example 30

Table 32, compiled from Tables 27, 29, and 31, compares the ethylene losses and the ethylene recovery rates of the process of the invention at varying stage-cuts. As can be seen, the higher the stage-cut, the lower is the ethylene loss in the argon vent stream, and the greater is the ethylene recovery. This result is in accordance with FIG. 7 and the calculations of Examples 18–24, which used a three-component feed mixture.

TABLE 32

| Parameter | No membrane | Table 27 | Table 29 | Table 31 |
| --- | --- | --- | --- | --- |
| Stage-Cut (%) | — | 80.3 | 87.0 | 91.2 |
| Ethylene concentration in vent stream (mol %) | 28.0 | 4.0 | 2.0 | 1.0 |
| Moles of ethylene lost/mole of argon vented | 2.8 | 0.22 | 0.10 | 0.05 |
| Removal/Recovery compared to No membrane (%) | — | 92.1 | 96.4 | 98.2 |

We claim:

1. A process for producing an organic product, comprising the following steps:
   (a) performing one or more reaction steps in a reaction zone to form the organic product, at least one of the reaction steps comprising a reaction of an organic feedstock chosen from the soup consisting of ethylene, propylene, iso-butane, toluene, cyclohexane, cumene, o-xylene and p-xylene, with oxygen,
   (b) withdrawing from the reaction zone a crude organic product stream comprising the organic product, the organic feedstock, and argon;
   (c) removing at least a portion of the organic product from the crude organic product stream to form a non-product stream;
   (d) providing a membrane having a feed side and a permeate side, and being selectively permeable to the organic feedstock over argon,
   (e) passing at least a portion of the non-product stream across the feed side under conditions in which there is a pressure drop from the feed side to the permeate side;
   (f) withdrawing from the feed side an argon-rich purge stream enriched in argon and depleted in the organic feedstock compared with the non-product stream;
   (g) withdrawing from the permeate side an organic-feedstock-rich permeate stream enriched in the organic feedstock and depleted in argon compared with the non-product stream;
   (h) recirculating at least a portion of the organic-feedstock-rich permeate stream to the reaction zone.

2. The process of claim 1, wherein the process is characterized by a stage-cut between the organic-feedstock-rich permeate stream and the non-product stream of at least about 30%.

3. The process of claim 1, wherein the membrane comprises a rubbery polymer.

4. The process of claim 1, wherein the membrane comprises silicone rubber.

5. The process of claim 1, wherein the membrane has an organic feedstock/argon selectivity of at least about 4.

6. The process of claim 1, wherein the organic-feedstock-rich permeate stream contains at least 50% of the organic feedstock that was present in the portion of the non-product stream.

7. The process of claim 1, wherein the organic-feedstock-rich permeate stream contains at least 70% of the organic feedstock that was present in the portion of the non-product stream.

8. The process of claim 1, wherein the organic-feedstock-rich permeate stream contains at least 90% of the organic feedstock that was present in the portion of the non-product stream.

9. The process of claim 1, wherein the non-product stream further comprises carbon dioxide and wherein at least a portion of the non-product stream is treated to remove carbon dioxide and then recirculated to the reaction zone.

10. The process of claim 1, wherein the non-product stream further comprises carbon dioxide and wherein said portion of the non-product stream is treated to at least partially remove carbon dioxide prior to carrying out step (e).

11. A process for treating a purge stream from an organic product manufacturing process, the purge stream comprising argon and an organic feedstock chosen from the group consisting of ethylene, propylene, iso-butane, toluene, cyclohexane, cumene, o-xylene and p-xylene, the process comprising the following steps:
   (a) providing a membrane having a feed side and a permeate side, and being selectively permeable to the organic feedstock over argon;
   (b) passing at least a portion of the purge stream across the feed side under conditions in which there is a pressure drop from the feed side to the permeate side;
   (c) withdrawing from the feed side an argon-rich stream enriched in argon and depleted in the organic feedstock compared with the purge stream;
   (d) withdrawing from the permeate side an organic-feedstock-rich permeate stream enriched in the organic feedstock and depleted in argon compared with the purge stream;
   (e) recirculating at least a portion of the organic-feedstock-rich permeate stream to the organic product manufacturing process.

12. The process of claim 11, wherein the process is characterized by a stage-cut between the organic-feedstock-rich permeate stream and the purge stream of at least about 30%.

13. The process of claim 11, wherein the membrane comprises a rubbery polymer.

14. The process of claim 11, wherein the membrane comprises silicone rubber.

15. The process of claim 11, wherein the membrane has an organic feedstock/argon selectivity of at least about 4.

16. The process of claim 11, wherein the organic-feedstock-rich permeate stream contains at least 50% of the organic feedstock that was present in the portion of the purge stream.

17. The process of claim 11, wherein the organic-feedstock-rich permeate stream contains at least 70% of the organic feedstock that was present in the portion of the purge stream.

18. The process of claim 11, wherein the organic-feedstock-rich permeate stream contains at least 90% of the organic feedstock that was present in the portion of the purge stream.

19. A process for producing an organic product, comprising the following steps:
(a) performing one or more reaction steps in a reaction zone to form the organic product, at least one of the reaction steps comprising a reaction of an organic feedstock chosen from the group consisting of ethylene, propylene, iso-butane, toluene, cyclohexane, cumene, o-xylene and p-xylene, with oxygen;
(b) withdrawing from the reaction zone a crude organic product stream comprising the organic product, the organic feedstock, and argon;
(c) removing at least a portion of the organic product from the crude organic product stream to form a non-product stream;
(d) compressing the non-product stream;
(e) providing a membrane having a feed side and a permeate side, and being selectively permeable to the organic feedstock over argon;
(f) passing at least a portion of the non-product stream across the feed side under conditions in which there is a pressure drop from the feed side to the permeate side;
(g) withdrawing from the feed side an argon-rich purge stream enriched in argon and depleted in the organic feedstock compared with the non-product stream;
(h) withdrawing from the permeate side an organic-feedstock-rich permeate stream enriched in the organic feedstock and depleted in argon compared with the non-product stream;
(i) recirculating at least a portion of the organic-feedstock-rich permeate stream to the compressing step.

20. The process of claim 19, wherein the process is characterized by a stage-cut between the organic-feedstock-rich permeate stream and the non-product stream of at least about 30%.

21. The process of claim 19, wherein the membrane comprises a rubbery polymer.

22. The process of claim 19, wherein the organic-feedstock-rich permeate stream contains at least 50% of the organic feedstock that was present in the portion of the non-product stream.

23. The process of claim 19, wherein the non-product stream further comprises carbon dioxide and wherein at least a portion of the non-product stream is treated to remove carbon dioxide and then recirculated to the reaction zone.

24. A process for producing an organic product, comprising the following steps;
(a) performing one or more reaction steps in a reaction zone to form the organic product, at least one of the reaction steps comprising a reaction of an organic feedstock chosen from the group consisting of ethylene, propylene, iso-butane, toluene, cyclohexane, cumene, o-xylene and p-xylene with oxygen;
(b) withdrawing from the reaction zone a crude organic product stream;
(c) passing the crude organic product stream to one or more purification steps to produce the organic product, the organic feedstock, and argon;
(d) removing the organic feedstock and the argon to form a non-product stream;
(e) providing a membrane having a feed side and a permeate side, and being selectively permeable to the organic feedstock over argon;
(f) passing at least a portion of the non-product stream across the feed side under conditions in which there is a pressure drop from the feed side to the permeate side;
(g) withdrawing from the feed side an argon-rich purge stream enriched in argon and depleted in the organic feedstock compared with the non-product stream;
(h) withdrawing from the permeate side an organic-feedstock-rich permeate stream enriched in the organic feedstock and depleted in argon compared with the non-product stream;
(i) recirculating at least a portion of the organic-feedstock-rich permeate stream to the one or more purifications steps.

25. The process of claim 24, wherein the process is characterized by a stage-cut between the organic-feedstock-rich permeate stream and the non-product stream of at least about 30%.

26. The process of claim 24, wherein the membrane comprises a rubbery polymer.

27. The process of claim 24, wherein the organic-feedstock-rich permeate stream contains at least 50% of the organic feedstock that was present in the portion of the non-product stream.

28. The process of claim 24, wherein the non-product stream further comprises carbon dioxide and wherein at least a portion of the non-product stream is treated to remove carbon dioxide and then recirculated to the reaction zone.

* * * * *

UNITED STATES PATENT AND TRADEMARK OFFICE
CERTIFICATE OF CORRECTION

PATENT NO. : 6,018,060
DATED : January 25, 2000
INVENTOR(S) : Richard W. Baker, Douglas Gottschlich It is certified that error appears in the above-indentified patent and that said Letters Patent is hereby corrected as shown below:

In claim 1, column 31, line 28, the word "soup" should read --group--.

Signed and Sealed this

Sixth Day of March, 2001

Attest:

NICHOLAS P. GODICI

Attesting Officer

Acting Director of the United States Patent and Trademark Office